US006800765B2

(12) United States Patent
Diwu et al.

(10) Patent No.: US 6,800,765 B2
(45) Date of Patent: Oct. 5, 2004

(54) FLUORESCENT PH INDICATORS FOR INTRACELLULAR ASSAYS

(75) Inventors: Zhenjun Diwu, Los Altos, CA (US); Jesse J. Twu, Cupertino, CA (US); Guoliang Yi, Sunnyvale, CA (US); Luke D. Lavis, Sunnyvale, CA (US); Yen-Wen Chen, San Francisco, CA (US); Kelly J. Cassutt, Somerset, NJ (US)

(73) Assignee: Molecular Devices Corporation, Sunnyvale, CA (US)

( * ) Notice: Subject to any disclaimer, the term of this patent is extended or adjusted under 35 U.S.C. 154(b) by 0 days.

(21) Appl. No.: 10/108,656

(22) Filed: Mar. 27, 2002

(65) Prior Publication Data

US 2003/0068668 A1 Apr. 10, 2003

Related U.S. Application Data

(60) Provisional application No. 60/309,800, filed on Aug. 2, 2001.

(51) Int. Cl.$^7$ ...................... C07D 311/82; C07D 407/00
(52) U.S. Cl. ....................................... 549/223; 549/280
(58) Field of Search ................................ 549/223, 280

(56) References Cited

FOREIGN PATENT DOCUMENTS

EP          0 025 912 A1      4/1981

OTHER PUBLICATIONS

*The Fluorescent Probe BCECF Has a Heterogenous Distribution in Sea Urchin Eggs*, Mozingo et al., Cell Biology International Reports, vol. 14, No. 8, pp. 689–699, Aug. 1990.
*A Novel In Vitro Screening Assay for Trypanocidal Activity Using the Fluorescent Dye BCECF–AM*, Obexer e al., Trop. Med. Parasitol, vol. 46, pp. 45–48, 1995.
*Fluorescent Characteristics and Pharmacokinetic Profiles of the Fluorescent Probe BCECF in Various Tissues: The Role of Blood Content*, Devoisselle et al., Photochemistry and Photobiology, vol. 64, No. 6. pp. 906–910, 1996.
*pH Indicators*, Haugland, Handbook of Fluorescent Probes and Research Chemicals, pp. 551–570, ©1996.
*Ratiometric Measurement of Intracellular pH of Cultured Cells With BCECF in a Fluorescence Multi–Well Pante Render*, Grant et al., In Vitro Cell Dev. Biol., vol. 33, pp. 256–260, Apr. 1997.

*BCECF in Single Cultured Cells: Inhomogeneous Distribution but Homogeneous Response*, Weinlich et al., The Journal of Experimental Biology, vol. 201, pp. 57–62, 1998.
*Analysis of the Uptake of the Fluorescent Marker 2',7'–bis–(2–carboxyethyl)–5(and–6)–carboxyfluo–rescein (BCECF) by Hydrogenosomes in Trichomonas vaginalis*, Scott et al., European Journal of Cell Biology, vol. 76, pp. 139–145, Jun. 1998.
*Fluorescence Probe (BCECF) Loading Efficiency in Human Platelets Depends on Cell Concentration: Application to pH Measurements*, Ruiz–Palomo et al., Clinical Biochemistry, vol. 32, No. 5, pp. 391–394, 1999.
*In Vivo Application of Intestinal pH Measurement Using 2',7'–Bis(carboxyethyl)–5,6–carboxyfluorescein (BCECF) Fluorescence Imaging*, Marechal et al., Photochemistry and Photobiology, vol. 70, No. 5, pp. 813–819, 1999.
*Acetoxymethyl (AM) and Acetate Esters*, Product Information, Molecular Probes, Inc., pp. 1–2, Mar. 5, 2001.
*BCECF*, Product Information, Molecular Probes, Inc., pp. 1–3, Mar. 6, 2001.
*Use of Fluorescent Dye BCECF to Measure Intracellular pH in cortical Collecting Tubule*, Weiner et al., Chemical Abstracts, vol. 111, No. 7, Abstract No. 53573f, 1989.
*Fluorescent Molecular Probes III. 2',7'–bis–(3–Carboxypropyl)–5–(nad–6)–Carboxyfluoresceint (BCPCF): A New Polar Dual–Excitation and Dual–Emission pH Indicator with a PKA of 7.0*, Liu et al.,Bioorganic & Medicinal Chemistry Letters, vol. 7, No. 23, pp. 3069–3072, 1997.
*Cell Determination Using Fluorescent Enzyme Substrates*, Kawasaki et al., Chemical Abstracts, vol. 129, No. 17, Abstract No. 213845y, 1998.
*Development of a Simple Cell Invasion Assay System*, Yamakawa et al., Biol. Pharm. Bull., vol. 23, No. 10, pp. 1264–1266, 2000.

Primary Examiner—Amelia A. Owens
(74) Attorney, Agent, or Firm—Kolisch Hartwelll, PC

(57) ABSTRACT

Systems, including compositions and methods, for measuring pH, particularly in cells, organelles, and other samples. The compositions include pH-sensitive fluorescent and fluorogenic 2',7'-dialkylfluorescein derivatives and associated nonfluorescent precursor compounds. The compositions may permit ratiometric measurement in the excitation spectrum and the emission spectrum. The methods include adding a precursor compound to a sample cell, incubating the sample cell to release the free indicator, illuminating the sample cell, and detecting the fluorescence response of the free indicator.

34 Claims, 6 Drawing Sheets

FLUORESCENT PH INDICATORS FOR INTRACELLULAR ASSAYS

CROSS-REFERENCES TO PRIORITY APPLICATIONS

This application is based upon and claims the benefit under 35 U.S.C. § 119 of the following U.S. provisional patent application, which is hereby incorporated by reference in its entirety for all purposes: Ser. No. 60/309,800, filed Aug. 2, 2001.

CROSS-REFERENCES TO ADDITIONAL MATERIALS

This application incorporates by reference in their entirety for all purposes the following U.S. Pat. No. 5,355,215, issued Oct. 11, 1994; U.S. Pat. No. 6,097,025, issued Aug. 1, 2000; and U.S. Pat. No. 6,159,425, issued Dec. 12, 2000.

This application incorporates by reference in their entirety for all purposes the following U.S. patent application Ser. No. 09/337,623, filed Jun. 21, 1999; Ser. No. 09/349,733, filed Jul. 8, 1999; Ser. No. 09/478,819, filed Jan. 5, 2000; Ser. No. 09/596,444, filed Jun. 19, 2000; Ser. No. 09/626,208, filed Jul. 26, 2000; Ser. No. 09/643,221, filed Aug. 18, 2000; Ser. No. 09/710,061, filed Nov. 10, 2000; Ser. No. 09/722,247, filed Nov. 24, 2000; Ser. No. 09/759,711, filed Jan. 12, 2001; Ser. No. 09/765,869, filed Jan. 19, 2001; Ser. No. 09/765,874, filed Jan. 19, 2001; Ser. No. 09/766,131, filed Jan. 19, 2001; Ser. No. 09/767,316, filed Jan. 22, 2001; Ser. No. 09/767,434, filed Jan. 22, 2001; Ser. No. 09/767,579, filed Jan. 22, 2001; Ser. No. 09/767,583, filed Jan. 22, 2001; Ser. No. 09/768,661, filed Jan. 23, 2001; Ser. No. 09/768,742, filed Jan. 23, 2001; Ser. No. 09/768,765, filed Jan. 23, 2001; Ser. No. 09/770,720, filed Jan. 25, 2001; Ser. No. 09/770,724, filed Jan. 25, 2001; Ser. No. 09/777,343, filed Feb. 5, 2001; Ser. No. 09/836,575, filed Apr. 16, 2001; Ser. No. 09/844,655, filed Apr. 27, 2001; Ser. No. 10/003,030, filed Oct. 29, 2001; Ser. No. 10/012,255, filed Nov. 12, 2001; Ser. No. 10/000,172, filed Nov. 30, 2001; and Ser. No. 10/061,416, filed Feb. 1, 2002.

This application incorporates by reference in their entirety for all purposes the following U.S. Provisional Patent Application Serial No. 60/223,642, filed Aug. 8, 2000; Serial No. 60/244,012, filed Oct. 27, 2000; Serial No. 60/250,683, filed Nov. 30, 2000; Serial No. 60/287,697, filed Apr. 30, 2001; Serial No. 60/316,704, filed Aug. 31, 2001; Serial No. 60/318,038, filed Sep. 7, 2001; and Serial No. 60/318,149, filed Sep. 7, 2001.

This application incorporates by reference in their entirety for all purposes the following publications: Richard P. Haugland, *Handbook of Fluorescent Probes and Research Chemicals* (6th ed. 1996); and Joseph R. Lakowicz, *PRINCIPLES OF FLUORESCENCE SPECTROSCOPY* (2nd Ed. 1999).

FIELD OF THE INVENTION

The invention relates to compositions and methods for measuring pH. More particularly, the invention relates to compositions and methods for measuring pH in cells, organelles, and other samples using fluorescent and fluorogenic 2',7'-dialkylfluorescein derivatives.

BACKGROUND OF THE INVENTION

The measurement of the pH of biological fluids is an important aspect of a variety of assays. In particular, intracellular pH plays an important modulating role in many cellular events, including cell growth, calcium regulation, enzymatic activity, receptor-mediated signal transduction, ion transport, endocytosis, chemotaxis, cell adhesion, and other cellular processes. The use of fluorescence-based techniques may increase the sensitivity of measurements and allow the measurement of intracellular pH in single cells, for example, by flow cytometry or existing fluorescence-based automated high-throughput microplate assays. Imaging techniques that use fluorescent pH indicators also may allow researchers to investigate these processes with much greater spatial resolution and sampling density than can be achieved using other available technologies, such as microelectrodes. Fluorescence assays are typically able to utilize low concentrations of the pH indicator, potentially reducing toxicity and buffering effects.

In selecting a pH indicator, to allow the greatest sensitivity to small changes in pH of the medium, the equilibrium constant between the acidic and basic forms of the indicator for the dye (i.e., the $pK_a$) should be near the pH of the selected assay medium. For physiological assays, such as blood and most intracellular fluid assays, the pH typically is in the range pH 6 to pH 8, and more typically in the range pH 6.5 to 7.6.

A variety of fluorescein-based pH indicators have been described, including fluorescein, carboxyfluorescein, fluorescein sulfonic acid, chloromethylfluorescein, carboxynaphthofluorescein, seminaphthorhodafluor derivatives, and seminaphthofluorescein derivatives. Typically, for intracellular assays, the dye is used as a cell-permeant diacetate derivative that is subsequently cleaved by nonspecific esterases within the cells of the sample, producing the active indicator.

Perhaps the most commonly utilized fluorescein-based pH indicator is 2',7'-bis-(2-carboxyethyl)-5-(and-6)-carboxyfluorescein, more commonly known as BCECF. BCECF has a $pK_a$ of 7.0, making it an ideal choice for intracellular assays. In addition, BCECF exhibits pH-dependent dual excitation and is excited efficiently by the 488-nm line of an argon-ion laser, as used in a variety of instruments. Ester derivatives of BCECF, most typically BCECF-AM, are nonfluorescent and membrane-permeant, and can be loaded into cells without disruption of the cell membranes. The conversion to the fluorescent version of the indicator can serve as an indicator of cell viability, as well as permitting subsequent pH measurements.

Unfortunately, for all its advantages, BCECF also possesses significant disadvantages. The synthesis of BCECF-AM typically produces a mixture of discrete compounds, as shown below in formulas I, II, and III.

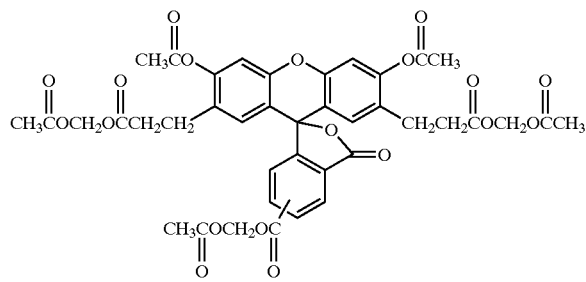

Formula I

-continued

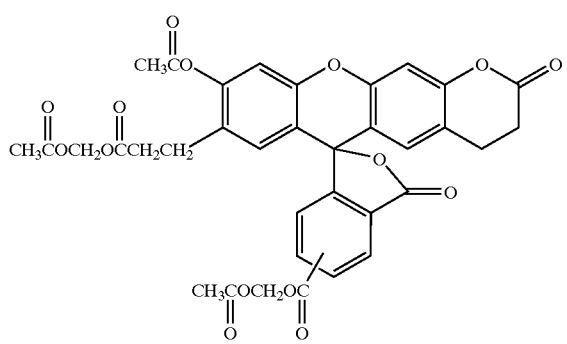

Formula II

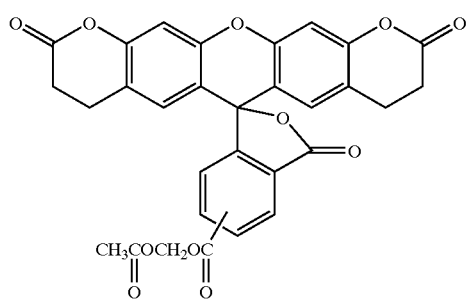

Formula III

This results in substantial variations in the ratios of active components and the profiles of impurities. Thus, different commercial sources of BCECF-AM commonly yield indicators of highly variable quality due to differences in their manufacturing processes. In fact, the quality often varies considerably from batch to batch even from a single manufacturer. The variation of component ratios has caused some difficulties in obtaining reproducible data due to the lack of consistent commercial material. In addition, the extremely weak excitation peak of BCECF at shorter wavelengths makes excitation-ratiometric measurements difficult, and it is impossible to perform emission-ratiometric pH measurements using BCECF due to the lack of pH-dependent dual emission. Thus, there is a need for improved fluorescent pH indicators, particularly for intracellular assays.

SUMMARY OF THE INVENTION

The invention provides systems including compositions and methods for measuring pH, particularly in cells, organelles, and other samples. The compositions include pH-sensitive fluorescent and fluorogenic 2',7'-dialkylfluorescein derivatives and associated nonfluorescent precursor compounds. The compositions may allow ratiometric measurement in the excitation spectrum and the emission spectrum. The methods include adding a precursor compound to a sample cell, incubating the sample cell to release the free indicator, illuminating the sample cell, and detecting the fluorescence response of the free indicator.

DETAILED DESCRIPTION

Figure 1:
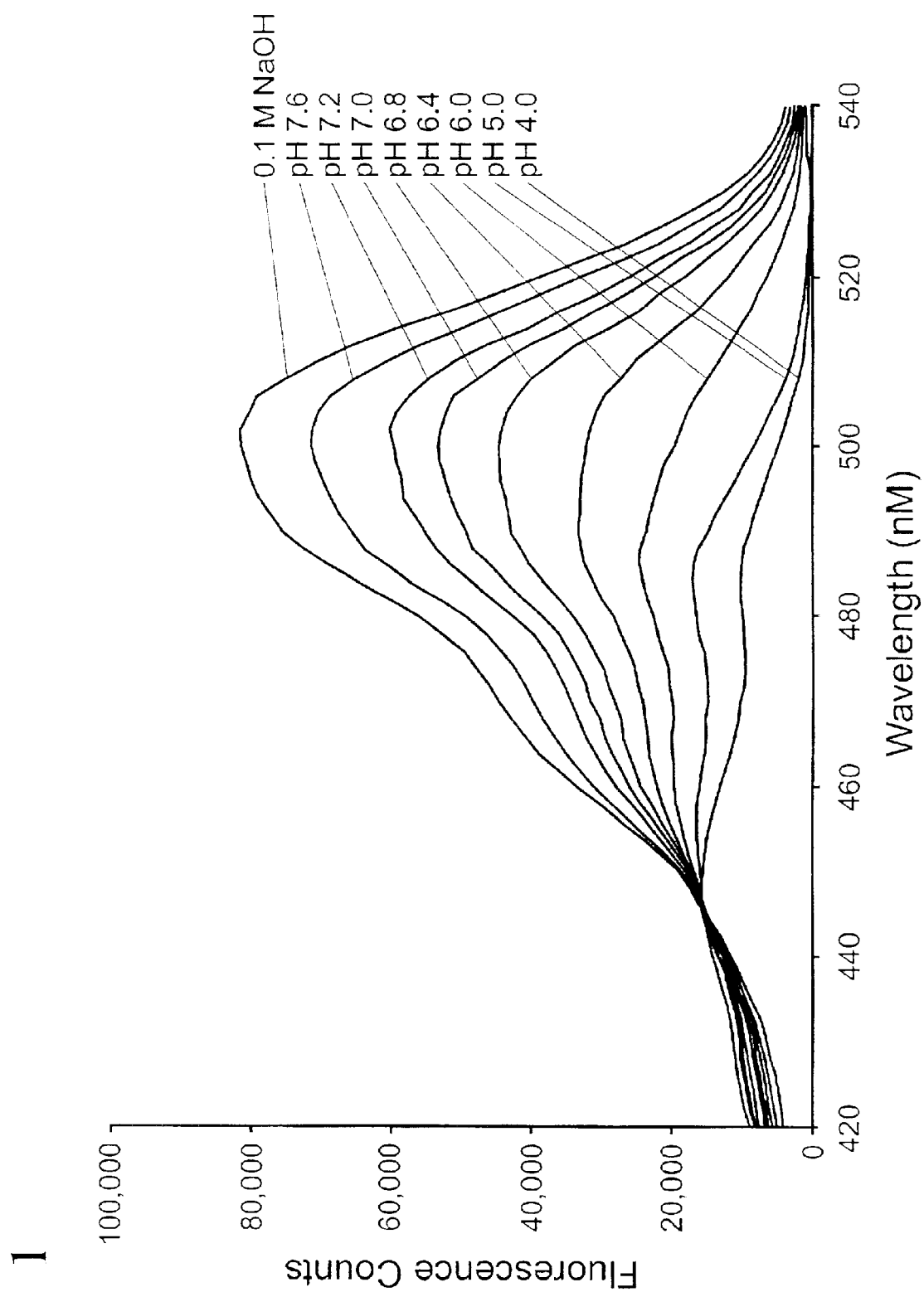
FIG. 1 shows the pH-dependence of the excitation spectrum of Compound 4 (as described in Example 15).

The invention provides systems including compositions and methods for measuring pH, particularly in cells, organelles, and other samples. The compositions include pH-sensitive fluorescent and fluorogenic 2',7'-dialkylfluoresceins derivatives and associated nonfluorescent precursor compounds. The methods include adding a precursor compound to a sample cell, incubating the sample cell to release the free indicator, illuminating the sample cell, and detecting the fluorescence response of the free indicator.

The compositions and methods may have various advantages. For example, the compositions may retain the advantageous spectral properties of BCECF while being readily prepareable as single components. Additionally, the compositions may be readily modifiable to make them suitable for applications in various cellular assays. The dyes may exhibit strong excitation-ratiometric properties and possess ratioable emission spectra that BCECF lacks. These ratioable emission spectra may be used for emission-ratiometric pH measurements in various biological systems. The dyes may be useful for staining live cells and measuring intracellular pH levels, in particular, for monitoring cell viability, cellular enzyme activity, and multi-drug resistance. The dyes of the invention also may be useful in various high-throughput screening methods, including flow cytometry, microplate assays, and microfluidic methods.

The following sections describe these and other aspects of the invention in more detail: (1) compositions, (2) applications, (3) synthesis, and (4) examples.

Compositions

The invention provides pH-sensitive fluorescent and fluorogenic 2',7'-diakylfluorescein derivatives and associated nonfluorescent precursors. The 2',7'-dialkylfluorescein derivatives include nonfluorescent precursors to fluorescent pH indicators that may be characterized according to the formula:

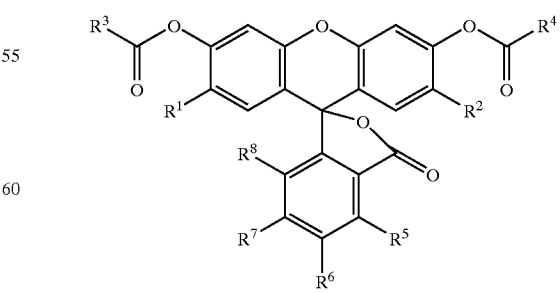

In the above formula, the substituents $R^1$ and $R^2$ are independently a $C_1$–$C_{12}$ alkyl that is optionally linear or branched, saturated or unsaturated. Typically, each of $R^1$ and $R^2$ is an unsubstituted alkyl, or is an alkyl substituted by one or more $C_1$–$C_6$ alkoxy groups. Alternatively, $R^1$ and $R^2$ are halogenated alkyl, provided that halogenation occurs at the beta-position (e.g., fluoroethyl, chloroethyl) or beyond the beta-position. Compounds where the $R^1$ and $R^2$ substituents are halogenated at the alpha-position (such as a chloromethyl substituent) typically exhibit reduced $pK_a$ values. In some embodiments, both of $R^1$ and $R^2$ are $C_1$–$C_6$ alkyl groups. In other embodiments, $R^1$ and $R^2$ are each methyl or ethyl, preferably ethyl.

The acyl substituents $R^3$ and $R^4$ are selected to form an ester that is readily cleavable by nonspecific intracellular esterase enzymes. Typically, $R^3$ and $R^4$ are $C_1$–$C_6$ alkyl groups. Preferably, both $R^3$ and $R^4$ are methyl groups. Where $R^3$ and $R^4$ are each methyl, the resulting compound is a 2',7'-dialkylfluorescein diacetate derivative.

The substituents $R^5$–$R^8$ are independently hydrogen, halogen, $C_1$–$C_6$ alkyl, $C_1$–$C_6$ alkoxy, sulfonic acid, or carboxylic acid. As used herein, "sulfonic acid" and "carboxylic acid" include the protonated functional group, the deprotonated and ionic functional group, and salts of the functional group. The carboxylic acid or sulfonic acid functional group is optionally "masked" or protected so as to render the resulting compound more cell-permeable. Typically, such protecting groups include esters of alcohols having 1–6 carbons or esters of acyloxyalkyl groups, preferably acetoxymethyl esters. Alternatively, one or more of $R^5$–$R^8$ is a reactive functional group, $R_X$, or a conjugated substance, $S_C$, that is bound via a covalent linking moiety L.

If one or more of $R^5$–$R^8$ is nonhydrogen, it typically is one or the other of $R^6$ and $R^7$. Derivatives of the dyes that are 5- or 6-carboxy derivatives or that are prepared from the 5- or 6-carboxy derivatives are particularly preferred, due to the ease of their synthesis. Although the compounds of the invention may be present as a mixture of 5- and 6-carboxy isomers or their derivatives, this mix of isomers should be distinguished from the mixture of distinct chemical compounds that typically is present when BCECF is prepared, as discussed above. In addition, methods are available, including high-resolution chromatographic methods, for separating the 5- and 6-substituted isomers of the compounds of the invention, according to methods known in the art.

Upon exposure to esterase enzymes, typically present within cells, or other suitable oxidizing conditions, the nonfluorescent spirolactone precursor compounds of the invention may be converted to fluorescent pH indicators having the formula:

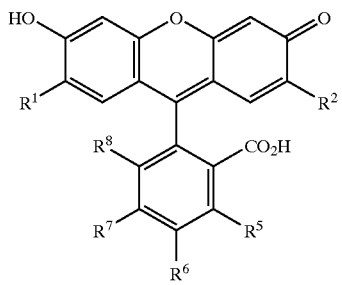

The substituents $R^1$ and $R^2$ of the indicators of the dyes of the invention are as defined above, as are substituents $R^5$–$R^8$, except that substituents that are protected or masked carboxylic acid or sulfonic acid functional groups may be no longer protected or masked. Esterase activity typically releases the free carboxylic acid or sulfonic acid.

The covalent linking moiety L is optionally a single covalent bond, such that either the reactive functional group $R_X$ or the conjugated substance $S_C$ is bound directly to the compound of the invention. Alternatively, L may incorporate a series of nonhydrogen atoms that form a stable linkage between the reactive functional group or conjugated substance and the compound. Typically, L incorporates 1–20 nonhydrogen atoms in a stable conformation. Stable atom conformations include, without limitation, carbon-carbon bonds, amide linkages, ester linkages, sulfonamide linkages, ether linkages, thioether linkages, and other covalent bonds well-known in the art. Preferred covalent linkages are single bonds, carboxamides, sulfonamides, ethers, and carbon-carbon bonds, or a combination thereof.

Any reactive functional group that exhibits appropriate reactivity to be conjugated with a desired substance is a suitable reactive functional group for the purposes of the invention. The choice of the reactive group used typically depends on the functional groups present on the substance to be conjugated. Typically, functional groups present on such substances include, but are not limited to, alcohols, aldehydes, amines, carboxylic acids, halogens, ketones, phenols, phosphates, and thiols, or a combination thereof. Suitable $R_X$ groups include activated esters of carboxylic acids, aldehydes, alkyl halides, amines, anhydrides, aryl halides, carboxylic acids, haloacetamides, halotriazines, hydrazines (including hydrazides), isocyanates, isothiocyanates, maleimides, phosphoramidites, sulfonyl halides, and thiol groups, or a combination thereof. Typically, $R_X$ is an activated ester of a carboxylic acid, an amine, a haloacetamide, a hydrazine, an isothiocyanate, or a maleimide group. In one aspect of the invention, $R_X$ is a succinimidyl ester of a carboxylic acid.

The compounds of the invention that have a covalently bound reactive functional group may be used to prepare a variety of conjugates. In one aspect of the invention, the conjugated substance is a member of a specific binding pair. In another aspect of the invention, the conjugated substance is a molecular carrier. In yet another aspect of the invention, the conjugated substance is a biomolecule that is an amino acid, a peptide, a protein, a nucleoside, a nucleotide, an oligonucleotide, a nucleic acid polymer, or a carbohydrate. In yet another aspect of the invention, the conjugated substance is a polar moiety, or a masked polar moiety. In yet another aspect of the invention, the conjugated substance is a solid or semi-solid matrix.

Where the conjugated substance $S_C$ is an amino acid, a peptide, a protein, a nucleoside, a nucleotide, an oligonucleotide, a nucleic acid polymer, or a carbohydrate, the conjugated substance may be a naturally occurring or a synthetically modified substance. The conjugated substance also may be a member of a specific binding pair or a molecular carrier. Specific binding pair members typically specifically bind to and are complementary with the complementary member of the specific binding pair. Conjugated members of a specific binding pair typically are used to localize the compound of the invention to the complementary member of that specific binding pair. Representative specific binding pairs are listed in Table 1.

TABLE 1

Representative specific binding pair members

| | |
|---|---|
| antibody | antigen |
| avidin (streptavidin) | biotin |
| DNA | aDNA |
| enzyme | enzyme substrate |
| lectin | carbohydrate |
| receptor | ligand |
| RNA | aRNA |

Where the conjugated substance $S_C$ is a carrier, it typically is a biological or artificial polymer. Biological polymers include proteins, carbohydrates, and nucleic acid polymers. Artificial polymers include polyethylene glycols and polymeric microparticles composed of polystyrene, latex, or other polymeric material. Preferably, a conjugated carrier is a carbohydrate that is a dextran, or amino-substituted dextran, or a polymeric microparticle. Such carriers are useful for altering the solubility of the compound, enhancing its retention within cell membranes, or decreasing its compartmentalization within cells.

Where the conjugated substance is a polar moiety, the conjugated substance is typically substituted one or more times by a highly polar functional group, such as a carboxylic acid or sulfonic acid. To improve loading into cells, the polar moiety typically is masked or protected, temporarily rendering it more lipophilic and therefore more cell-permeant. One such masking group is an ester group that is cleaved by esterases to release the free polar moiety within cell membranes, where they are well-retained. Typically, the polar moiety is a carboxylic acid, a dicarboxylic acid, or a tricarboxylic acid moiety that is protected as an ester, typically as an acetoxymethyl ester.

Where the conjugated substance is a solid or semi-solid matrix, the conjugated substance may be a metal or glass surface, and may be, for example, the sides or bottom of a microwell, or a slide, or the surface of a chip. The compound of the invention is optionally covalently bound to a fiber optic probe, where the probe is composed of glass or functionalized glass (e.g., aminopropyl glass), or the compound is attached to the fiber optic probe via an intermediate polymer, such as polyacrylamide. Incorporation of the compounds of the invention on such surfaces permit the remote sensing of sample pH values.

Applications

The fluorescent compounds of the invention may be useful pH indicators, and particularly useful intracellular pH indicators. The compounds of the invention therefore typically are used to stain samples that contain cells. The sample typically is stained by passive means, i.e., by incubation of the desired sample with a staining solution containing the selected compound of the invention. Passive incubation is most useful for compounds of the invention that have been masked or protected and that therefore are nonpolar and cell-permeable. However, any other suitable method of introducing the compound of the invention into the sample, such as microinjection, can be used to aid or accelerate introduction of the dye into the sample. The nonfluorescent precursor compounds of the invention generally are most useful for staining cells, as they may be readily cell-permeant and converted to the fluorescent pH indicator within the cell membrane.

Before use, a staining solution of the compound of the invention is prepared. The compound of the invention typically is first dissolved in an organic solvent, such as DMSO or DMF, to prepare a concentrated stock solution. The stock solution is then diluted in the appropriate aqueous solution, typically a buffer solution, to prepare the staining solution for addition to the sample. The nonfluorescent spirolactone compounds of the invention typically are less soluble in aqueous solutions than the free fluorescent versions.

The sample is optionally combined with other solutions in the course of staining, such as wash solutions or solutions containing additional detection reagents. An additional detection reagent is a reagent that produces a detectable response due to the presence of a specific cell component, intracellular substance, or cellular condition, according to methods generally known in the art. Where the additional detection reagent has spectral properties that differ from those of the subject indicators, multi-color applications are possible.

Typically, after the compound of the invention is added to the sample, the sample is incubated for a time sufficient for intracellular esterases to convert the nonfluorescent spirolactone form of the dye to the fluorescent form of the dye. If the compound added to the sample already is in its fluorescent form, the sample need only be incubated for a time sufficient for the indicator compound to register a detectable fluorescence response to the pH of the sample. At any time after sufficient fluorescent dye is present in the sample to measure a detectable fluorescence signal, the sample may be illuminated and the resulting fluorescence detected.

Typically, the sample is illuminated at a wavelength of light that results in a detectable fluorescence response, and observed with a means for detecting the optical response. The illumination source typically is selected so that efficient excitation of the free compound is achieved. Useful illumination sources include ultraviolet or visible wavelength emission lamps, arc lamps, or lasers. These illumination sources are optionally integrated into laser scanners, fluorescence microplate readers, standard or mini fluorometers, flow cytometers, fluorescence microscopes, or chromatographic detectors. The fluorescence emission is optionally detected by visual inspection or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, any of which may optionally incorporate photomultiplier tubes to enhance the detectable fluorescence signal.

The compounds of the invention are particularly well suited for high-throughput screening techniques, particularly those involving automated methods and small sample volumes. In one aspect of the invention, the sample is illuminated, and the resulting fluorescence is detected using a fluorescence microplate reader, a flow cytometer, or a fluorescence microscope. The use of the compounds of the invention is particularly advantageous when performed using a fluorescence multiwell microplate reader.

The observation of a detectable change in the fluorescence properties of the compound of the invention in the sample typically is correlated with the pH of the sample. The correlation typically is accomplished by comparison of the fluorescence response to a standard, or calibration, curve. The standard curve is generated according to methods known in the art using various and known pH levels, or by comparison with a reference dye or dyed particle that has been standardized versus a known pH level.

The pH response of the free compounds of the invention may be determined using any suitable mechanism. In one embodiment, the pH response is determined by observing changes in the excitation or emission spectra at a single wavelength. In another embodiment, the pH response is determined by measuring the ratio of the excitation spectra at two different wavelengths. In yet another embodiment, the pH response is determined using the ratio of the fluorescence emission spectra at two different wavelengths. Ratiometric measurements may reduce spurious changes in the signal, such as those due to photobleaching, nonuniform indicator distribution, variable sample thickness, etc. It is helpful to subtract background fluorescence levels from the two component fluorescence intensities before calculation of a ratiometric value.

The compounds of the invention may be provided in the form of kits for measuring pH values or determining pH responses. These kits optionally may include chemically reactive forms of the compounds to permit a user to label substances of interest and develop individual assays. Alternatively, the kits may include conjugates of the compound that are selected specifically for a particular assay, typically where the conjugated substance is a member of a specific binding pair. The kit optionally incorporates additional reagents, including but not limited to buffering agents, fluorescence calibration standards, enzymes, enzyme substrates, nucleic acid stains, labeled antibodies, and/or other additional fluorescence detection reagents. The compounds of the invention optionally are present in pure form as a lyophilized solid, or as a concentrated stock solution, or in a prediluted solution ready for use in the appropriate assay. Typically, the kit is designed for use in an automated and/or high-throughput assay, and so is designed to be fully compatible with microplate readers, microfluidic methods, and/or other automated high-throughput methods.

The assays of the invention optionally may be performed using apparatus, methods, and/or compositions described in the various patents and patent applications listed above under Cross-References and incorporated herein by reference. The apparatus include luminescence detectors and sample holders such as microplates, among others. The methods include photoluminescence methods, such as fluorescence intensity, among others. The compositions include various energy transfer donors and acceptors, among others.

Synthesis

The compounds of the invention may be prepared by any suitable method, including condensation of the appropriate resorcinol (such as 4-ethyl resorcinol) with various derivatives of phthalic acid or phthalic anhydride or sulfobenzoic acid or anhydride, or with benzaldehydes (when followed by oxidation), as described in more detail in the examples below. The condensation reaction typically occurs in the presence or absence of various acid catalysts and after an aqueous workup yields the desired substituted fluorescein.

Unsymmetrical fluorescein dyes may be prepared using any suitable method. For example, unsymmetrical dyes may be prepared by condensing one equivalent each of two different resorcinols with one equivalent of the appropriate phthalic acid derivative or benzaldehyde using acid catalysis. The desired unsymmetrical fluorescein dye may then be separated from any unwanted symmetrical dye side-product using chromatographic techniques well-known in the art. Alternatively, unsymmetrical dyes maybe prepared in a more stepwise manner by condensing a selected resorcinol with one equivalent of the appropriate phthalic acid derivative or benzaldehyde, isolating the resulting benzophenone derivative, and then condensing it with a different resorcinol to yield the asymmetric dye.

Post-condensation modifications of fluorescein dyes are well known in the art. In particular, the conversion of amino, hydroxy, and carboxy derivatives of fluoresceins to a wide variety of other reactive derivatives may be accomplished using standard synthetic methods. These reactive derivatives in turn can be conjugated to amino acids, peptides, proteins, nucleotides, oligonucleotides, nucleic acids, carbohydrates, and other substances of interest using standard conjugation chemistry.

Exemplary synthetic strategies for selected 2',7'-dialkylfluoresceins are described below, under Examples.

EXAMPLES

The following examples describe selected aspects and embodiments of the invention, including methods for preparing and using selected pH indicators. These examples are included for illustration and are not intended to limit or define the entire scope of the invention.

Example 1

Preparation of 2',7'-diethyl-5-(or 6-) Carboxyfluorescein Diacetate (Compound 3)

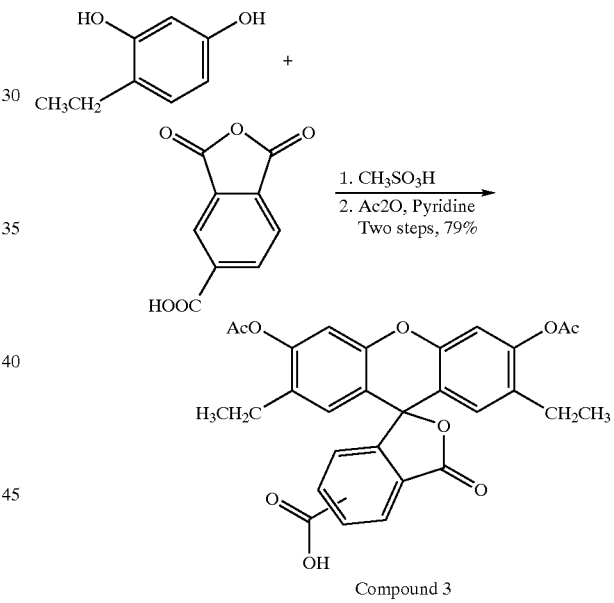

Compound 3

A mixture of 4-ethylresorcinol (2.76 g, 20 mmol) and 1,2,4-benzenetricarboxylic anhydride (1.92 g, 10 mmol) in methanesulfonic acid (20 mL) is stirred under nitrogen at 80–81° C. for 17 hours. The cooled reaction mass is poured into ice/water (140 mL) followed by filtration. The solid is dissolved in ethyl acetate, and additional water is removed with a separation funnel. The organic layer is washed with 15 ml of brine, filtered, and concentrated to yield a crude yellow solid (4.32 g).

A solution of the above crude intermediate (4.32 g, 10 mmol) in acetic anhydride (42 mL) is heated at 80° C. in the presence of pyridine (45 mL) for 30 minutes. The reaction mixture is cooled to room temperature and concentrated in vacuo at 30° C. The residue is dissolved in methylene chloride and washed with 3% cold hydrochloric acid (three times) and water. The organic layer is dried over anhydrous magnesium sulfate, and evaporated to dryness. The crude product is purified on a silica gel column with solvents of ethyl acetate/methylene chloride (1:50, 1:20, 1:10) as an eluent to yield the desired 2',7'-diethyl-5-(or 6-) carboxyfluorescein diacetate (4.10 g, yield: 79%). A repeated recrystallization from ethyl acetate/methanol (followed by further HPLC purification) gives the pure 5- and 6-isomers (Compound 3).

Example 2

Preparation of 2',7'-diethyl-5-(or 6-) Carboxyfluorescein (Compound 4)

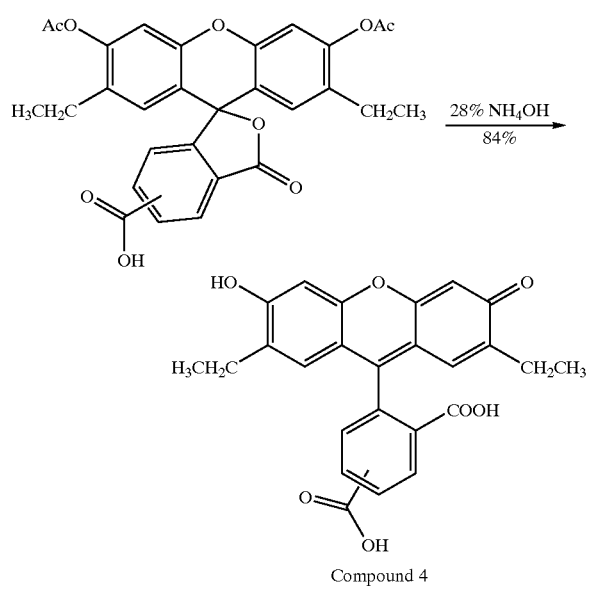

Compound 4

A solution of 2',7'-diethyl-5-(or 6-) carboxyfluorescein diacetate (Compound 3; 4.10 g, 7.9 mmol) in 10:10:1 tetrahydrofuran/methanol/water (130 ML) is stirred in the presence of 28% ammonium hydroxide (8 mL) at room temperature for 2 hours. The reaction mixture is poured into cold water (250 mL). The aqueous solution is acidified to pH 2 with 10% hydrochloric acid and filtered to collect the formed yellow precipitate. The solid is washed with cold water and dried under vacuum at 60° C. to give 2',7'-diethyl-5-(or 6-) carboxyfluorescein (Compound 4; 3.17 g, yield: 93%).

Example 3

Preparation of 2',7'-diethyl-5-(or 6-) Carboxyfluorescein Diacetate, Acetoxymethyl Ester (Compound 5)

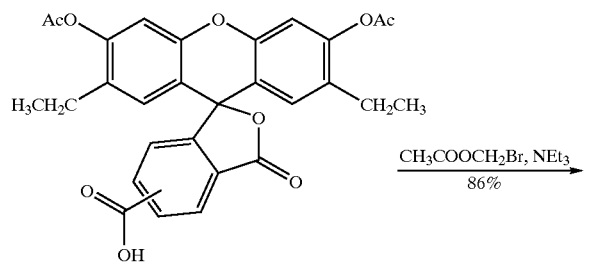

Compound 5

A solution of 2',7'-diethyl-5-(or 6-) carboxyfluorescein diacetate (Compound 3; 0.103 g, 0.2 mmol) and bromomethyl acetate (0.092 g, 0.6 mmol) in 1:1 methylene chloride/tetrahydrofuran (20 mL) is stirred at room temperature in the presence of triethylamine (0.067 g, 0.6 mmol) for 22 hours. The reaction mass is diluted with methylene chloride and washed twice with water. The organic layer is dried over anhydrous magnesium sulfate and evaporated to dryness. The crude product is purified on a silica gel column to give 2',7'-diethyl-5-(or 6-) carboxyfluorescein diacetate, acetoxymethyl ester (0.101 g, yield: 86%).

Example 4

Preparation of 2',7'-diethylfluorescein-5-(or 6-) Carboxylic Acid Succinimidyl Ester (Compound 6)

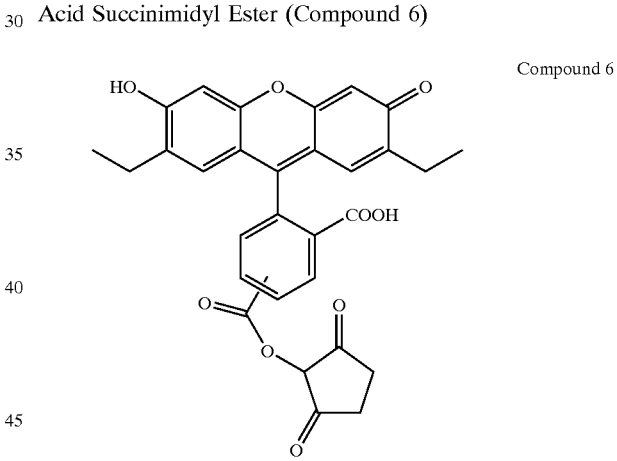

Compound 6

A 25 mL flask is equipped with a stirring bar and septum and flushed with dry $N_2$. The flask is charged with a solution of Compound 4 (110 mg, 0.245 mmol) in 2:1 anhydrous DMF/pyridine (2.0 mL). Succinimidyl trifluoroacetate (161 mg, 0.763 mmol) is added to the resulting yellow solution at once. The reaction mixture is stirred at room temperature for 3 hours, after which the entire mixture is poured into pH 5.0 buffer (50 mL). The resulting aqueous suspension is extracted with ethyl acetate (3×100 mL), and the combined organic layers are washed with water (1×50 mL) and brine (1×50 mL) and dried over $Na_2SO_4$. Removal of the solvent in vacuo affords an orange solid (~170 mg). The crude product is directly used for reactions in the following examples.

Example 5

Preparation of 2',7'-diethylfluorescein-5-(or 6-) Carboxylic Amide Nitrilotriacetic Acid (Compound 7)

Compound 7

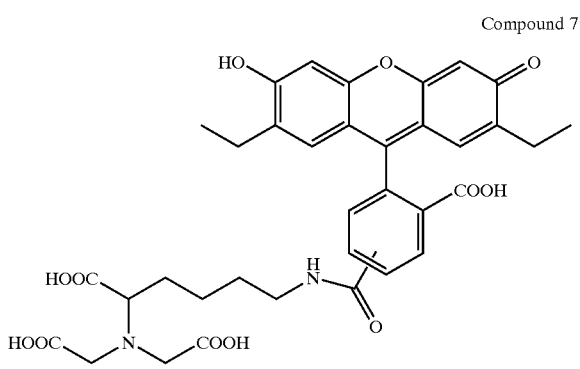

Compound 6 (110 mg) is taken up into 3.0 mL of anhydrous THF and placed in a 15 mL flask. To the resulting pale yellow solution are added 3.0 mL of water containing N-(5-amino-1-carboxypentyl)iminodiacetic acid (80 mg, 0.305 mmol) and $Na_2CO_3$ (103 mg, 1.22 mmol). The resulting mixture is stirred at room temperature for 22 hours. The reaction solution is concentrated in vacuo, and the residue is purified on a SEPHADEX LH-20 resin column using 100% $H_2O$ as eluent. The fractions containing the desired product are combined and lyophilized to yield 2',7'-diethylfluorescein-5-(or 6-) carboxylic amide, nitrilotriacetic acid (Compound 7) as orange crystals (160 mg, yield: 93%).

Example 6
Preparation of 2',7'-diethylfluorescein Diacetate-5-(or 6-) Carboxylic Amide, Nitrilotriacetic Acid, Trisacetoxymethyl Ester (Compound 8)

Compound 8

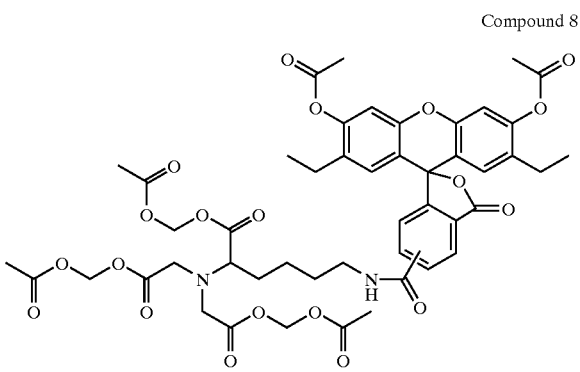

A 10 mL flask is equipped with a stirring bar and reflux condenser. The flask is then charged with Compound 7 (80 mg, 0.129 mmol), followed by addition of acetic anhydride (2.0 mL) and anhydrous pyridine (1.0 mL). The reaction mixture is stirred at 80° C. for 1 hour, after which the majority of solvent is removed in vacuo, and the resulting mixture is poured into 0.3 M HCl solution (5.0 mL). The resulting suspension is frozen and lyophilized to give a pale yellow solid. The solid is dissolved in anhydrous DMF (3.0 mL) containing diisopropylethylamine (0.3 mL). To the resulting solution is added bromomethyl acetate (152 μL, 237 mg, 1.55 mmol). The resulting mixture is stirred at room temperature for 48 hours under a dry $N_2$ atmosphere. After removal of the DMF and pyridine in vacuo, the residue is taken up into pH 5.0 buffer (30 mL). The resulting aqueous suspension is extracted with ethyl acetate (3×75 mL), and the combined organic layers are washed with water (1×30 mL) and brine (1×30 mL) and dried over $Na_2SO_4$. Evaporation of the solvent in vacuo affords a gummy brown residue (~50 mg). The crude residue is further purified on a silica gel flash column (9:1 $CHCl_3$/EtOAc as eluent) to afford 2',7'-diethylfluorescein diacetate-5-(or 6-) carboxylic amide, nitrilotriacetic acid, trisacetoxymethyl ester (Compound 8) as a light brown solid (22 mg, yield: 18%).

Example 7

Preparation of 2',7'-diethylfluorescein-5-(or 6-) Carboxylic Amide Diethyl Aminomalonate (Compound 9)

Compound 9

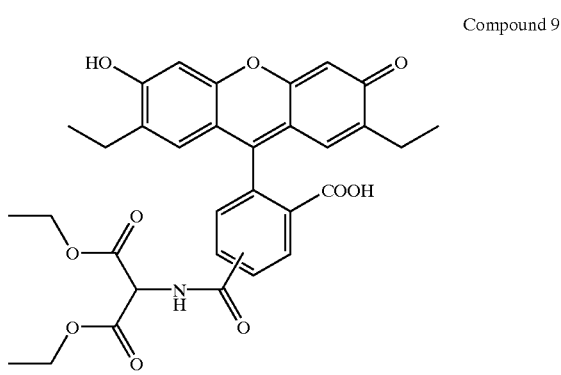

A 25 mL flask is equipped with stirring bar and septum and is flushed with dry $N_2$. The flask is charged with a solution of Compound 4 (400 mg, 0.925 mmol) in anhydrous DMF (2.0 mL) and anhydrous pyridine (1.0 mL). To the resulting yellow solution is added succinimidyl trifluoroacetate (976 mg, 4.63 mmol) at once. The reaction mixture is stirred at room temperature for 30 minutes, after which the entire mixture is poured into pH 5.0 buffer (50 mL). The resulting suspension is extracted with ethyl acetate (3×100 mL), and the combined organic layers are washed with water (1×50 mL) and brine (1×50 mL) and dried over $MgSO_4$. Evaporation of the solvent in vacuo affords an orange solid. The compound is dissolved in anhydrous DMF (4.0 mL). To the resulting yellow/orange solution is added triethylamine (425 μL, 309 mg, 3.05 mmol) followed by diethyl aminomalonate (587 mg, 2.77 mmol). The resulting mixture is stirred at room temperature for 24 hours. The reaction solution is concentrated in vacuo, and the residue is taken up into $H_2O$ (80 mL). The resulting suspension is extracted with ethyl acetate (3×125 mL), and the combined organic layers are washed with water (1×80 mL) and brine (1×80 mL) and dried over $MgSO_4$. Evaporation of the solvent in vacuo afforded an orange solid. The crude material is further purified on a silica gel flash column (20:1 $CHCl_3$/MeOH→5:1 $CHCl_3$/MeOH as eluent) to afford 2',7'-diethylfluorescein-5-(or 6-) carboxylic amide, diethyl aminomalonate (compound 9) as an orange solid (407 mg, yield: 73%).

Example 8

Preparation of 2',7'-diethylfluorescein-5-(or 6-) Carboxylic Amide, Aminomalonic Acid (Compound 10)

Compound 10

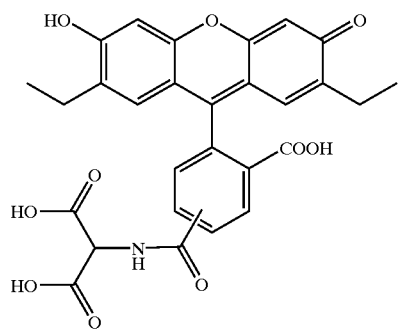

A 50 mL flask is equipped with a stirring bar and charged with Compound 9 (96 mg, 0.163 mmol) and 0.15 M NaOH solution (20 mL). The reaction mixture is stirred at room temperature for 24 hours, after which the pH is adjusted to ~5.0 by addition of 1.0 M HCl. The resulting solution is frozen and lyophilized to give 2',7'-diethylfluorescein-5-(or 6-) carboxylic amide, diethyl aminomalonic acid (Compound 10) as a pale yellow solid.

Example 9

Preparation of 2',7'-diethylfluorescein-5-(or 6-) Carboxylic Amide, N-(5-amino-1-carboxypentyl)Iminodiacetic Acid (Compound 11)

Compound 11

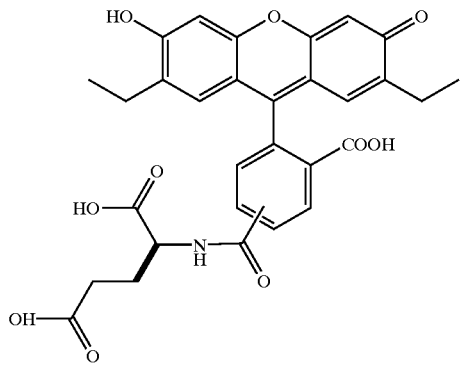

Compound 11 is prepared using a procedure analogous to the procedure of Example 5 for the preparation of Compound 7, except that glutamic acid is used instead of N-(5-amino-1-carboxypentyl)iminodiacetic acid.

Example 10

Preparation of 2',7'-diethyl-5-(or 6-) Chlorosulfonyl Fluorescein (Compound 12)

Compound 12

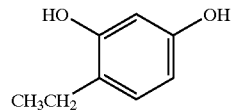
+

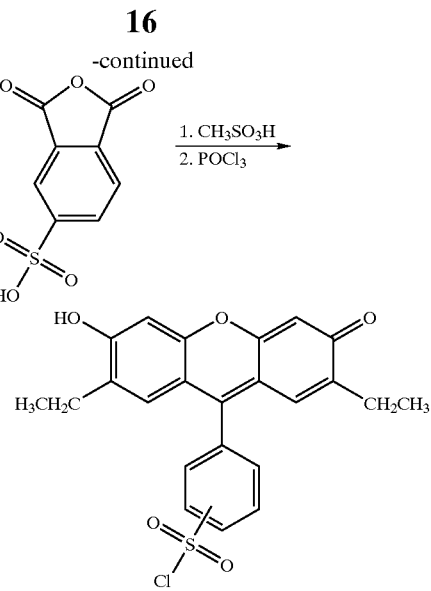

Compound 12 is prepared using a procedure analogous to the procedure of Example 1. 1,4-Ethylresorcinol is condensed with 5-sulfophthalic anhydride to give 2',7'-diethyl-5-(or 6-) sulfofluorescein. The sulfofluorescein is converted into the corresponding sulfonyl chloride as described by J. March (Advanced Organic Chemistry, $4^{th}$ ed., p 499, 1992), which is incorporated herein by reference.

Example 11

Preparation of 2',7'-diethylfluorescein-5-(or 6-) Isothiocyanate (Compound 14)

Compound 14

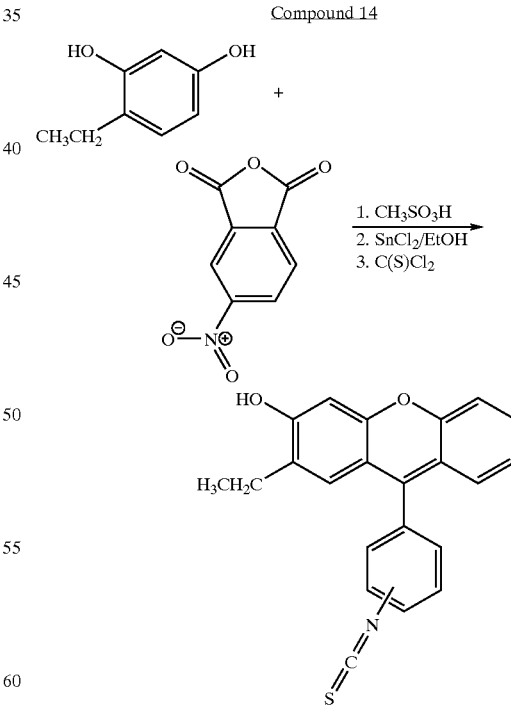

Compound 14 is prepared using a procedure analogous to the procedure of Examples 1 and 10. 1,4-ethylresorcinol is condensed with 5-nitrophthalic anhydride to give 2',7'-diethyl-5-(or 6-) nitro fluorescein. The nitrofluorescein is reduced to 2',7'-diethyl-5-(or 6-) aminofluorescin, which is then air-oxidized to the corresponding fluorescein. The aminofluorescein is converted into the corresponding isothiocyanate as described by J. March (Advanced Organic Chemistry, 4th ed., pp 417–418, 1992), which is incorporated herein by reference.

Example 12

Preparation of 2',7'-dimethyl-5-(or 6-)Carboxyfluorescein Diacetate (Compound 15), 2',7'-didodecyl-5-(or 6-)Carboxyfluorescein Diacetate (Compound 16), 2',7'-di-tert-butyl-5-(or 6-)Carboxyfluorescein Diacetate (Compound 17), and 2',7'-di(2-methoxyethyl)-5-(or 6-)Carboxyfluorescein Diacetate (Compound 18)

The following compounds are prepared from the condensation of corresponding resorcinols using procedures analogous to the procedures of Examples 1, 10, and 11.

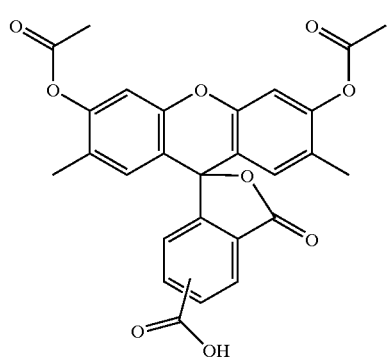

Compound 15

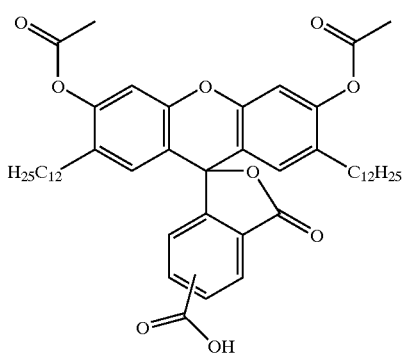

Compound 16

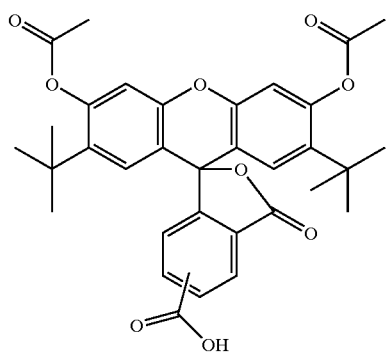

Compound 17

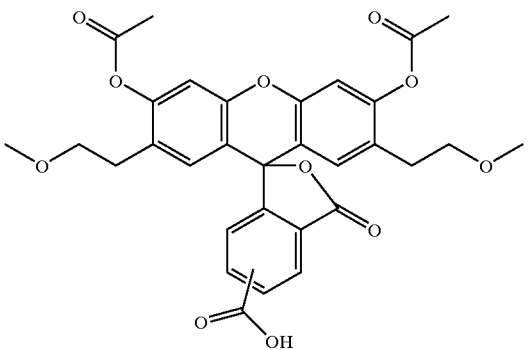

Compound 18

Example 13
Preparation of 2',7'-diethyl-5-Carboxyfluorescein Diacetate, Acetoxymethyl Ester (Compound 19)

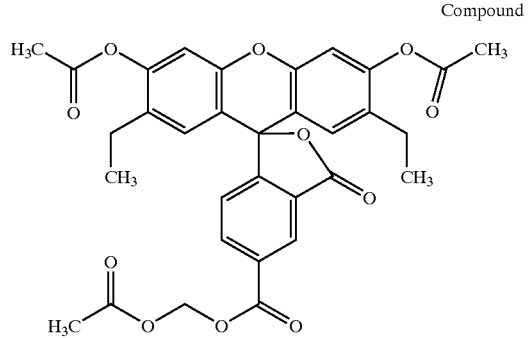

Compound 19

A solution of 2',7'-diethyl-5-carboxyfluorescein diacetate (0.1 g, 0.2 mmol) and bromomethyl acetate (0.09 g, 0.6 mmol) in 1:1 methylene chloride/tetrahydrofuran (20 mL) is stirred at room temperature in the presence of triethylamine (0.067 g, 0.6 mmol) for 24 h. The reaction mixture is diluted with methylene chloride and washed twice with water. The organic layer is dried over anhydrous magnesium sulfate, and evaporated to dryness. The crude product is purified on a silica gel column to give 2',7'-diethyl-5-carboxyfluorescein diacetate, acetoxymethyl ester (Compound 19; 0.1 g, yield: 86%).

Example 14
Preparation of 2',7'-diethyl-6-carboxyfluorescein Diacetate, Acetoxymethyl Ester (Compound 20)

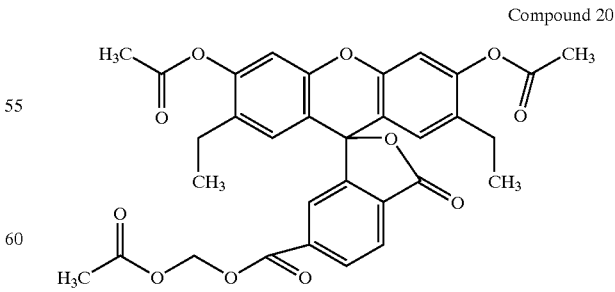

Compound 20

Compound 20 is prepared using a procedure analogous to the procedure described in Example 13 to prepare Compound 19, except that 2',7'-diethyl-6-carboxyfluorescein diacetate is used as a starting material.

Example 15
pH Titration of 2',7'-diethyl-5-(or 6-)Carboxyfluorescein (Compound 4)

Figure 2:
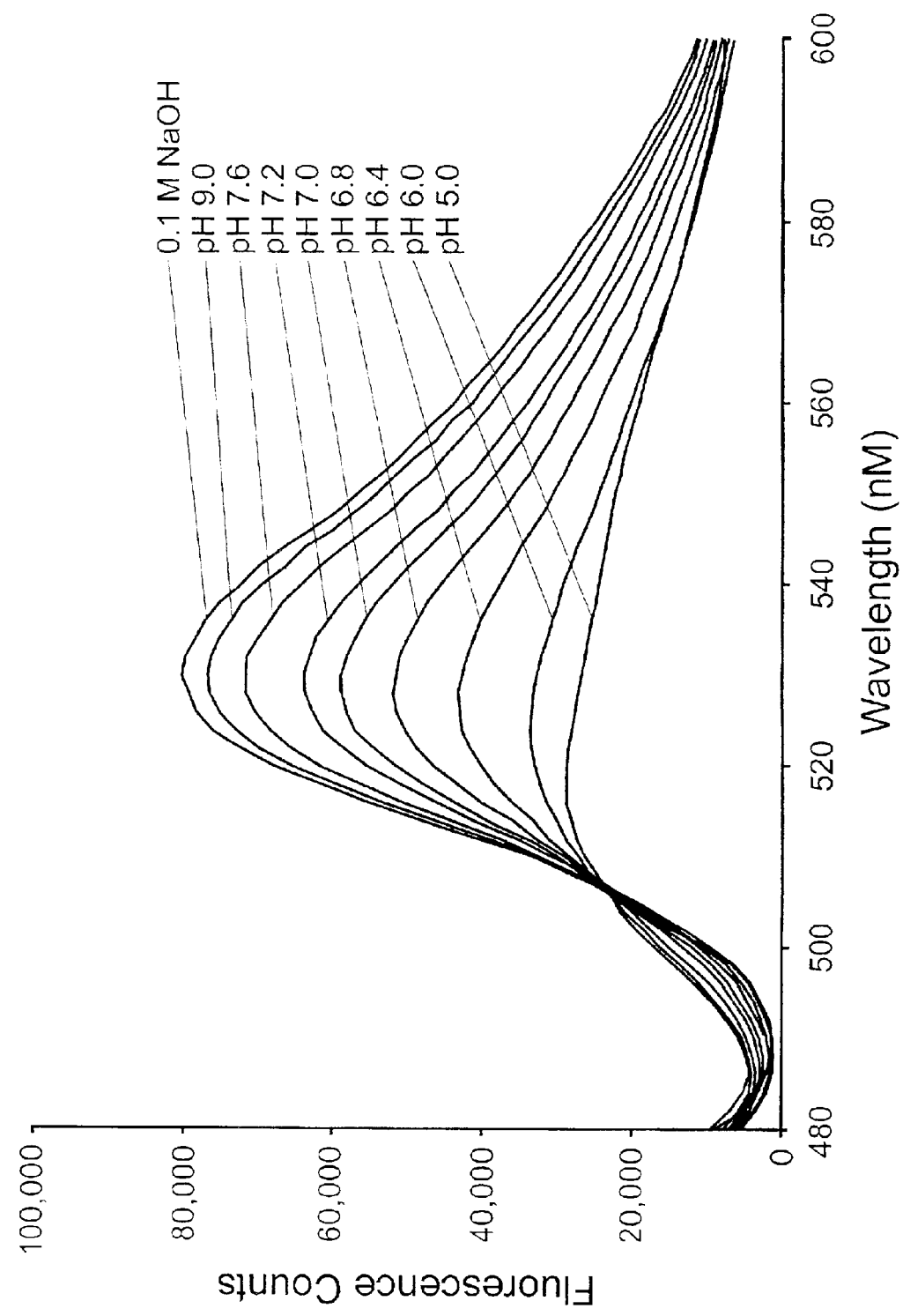
FIG. 2 shows the pH-dependence of the fluorescence emission spectrum of Compound 4 (as described in Example 15).

A 1 mM DMSO stock solution of 2',7'-diethyl-5-(or 6-)carboxyfluorescein is diluted with a series of different pH buffers (final concentration=1.0 µM). The excitation and emission spectra of the aqueous solutions are obtained with a Gemini XS fluorescence plate reader (Molecular Devices Corporation; Sunnyvale, Calif.). As shown in FIGS. 1 and 2, Compound 4 has both dual excitation and dual emission with a calculated pKa (acid dissociation constant) of 6.96. These characteristics make the compound an ideal pH probe to measure intracellular pH changes in various biological systems in either a single wavelength mode or in a ratiometric measurement mode. In summary, Compound 4 retains all of the ideal spectral properties of BCECF-AM. Additionally, the compound is present as a single component and can be readily modified for various cellular applications. It has stronger excitation-ratiometric properties than BCECF and a ratioable emission spectra that BCECF lacks.

Example 16
Monitoring Intracellular pH Fluctuation Using Compounds 5, 8, or 20 in Combination with a Fluorescence Imaging Plate Reader (FLIPR®) System Approximately 60,000 CHO-M1 cells are plated in 100 µL of Ham's F-12 medium/10% fetal bovine serum (FBS) per well of a 96-well plate and incubated at 37° C. in a humidified $CO_2$ incubator for overnight. A 5× loading buffer is prepared by mixing 10 µL of the 10 mM Compound 5, 8, or 20 stock solution (in DMSO) to 2 mL of 1× Hank's balanced salt solution (HBSS) buffered with 20 mM HEPES (pH 7.40) (H+H Buffer) and 12.5 mM probenecid. Cell plates are removed from the incubator. 60 µL of medium is removed, 10 µL of the 5× loading buffer is added, and the cell plates are incubated at 37° C. for 1 hour. An acute acid-load procedure is performed as follows. 5 µL of 220 mM $NH_4Cl$ in H+H Buffer/2.5 mM probenecid is added per well, and the cell plates are incubated at 37° C. for an additional 15 minutes. Cell plates are then placed on the FLIPR® instrument. A two-addition mode is set for the FLIPR® instrument, with a first addition of 200 µL of H+H Buffer/2.5 mM probenecid, followed by a second addition of 36 µL of the agonist carbachol in 4.3 mM $NH_4Cl$/H+H buffer/2.5 mM probenecid.

Figure 3:
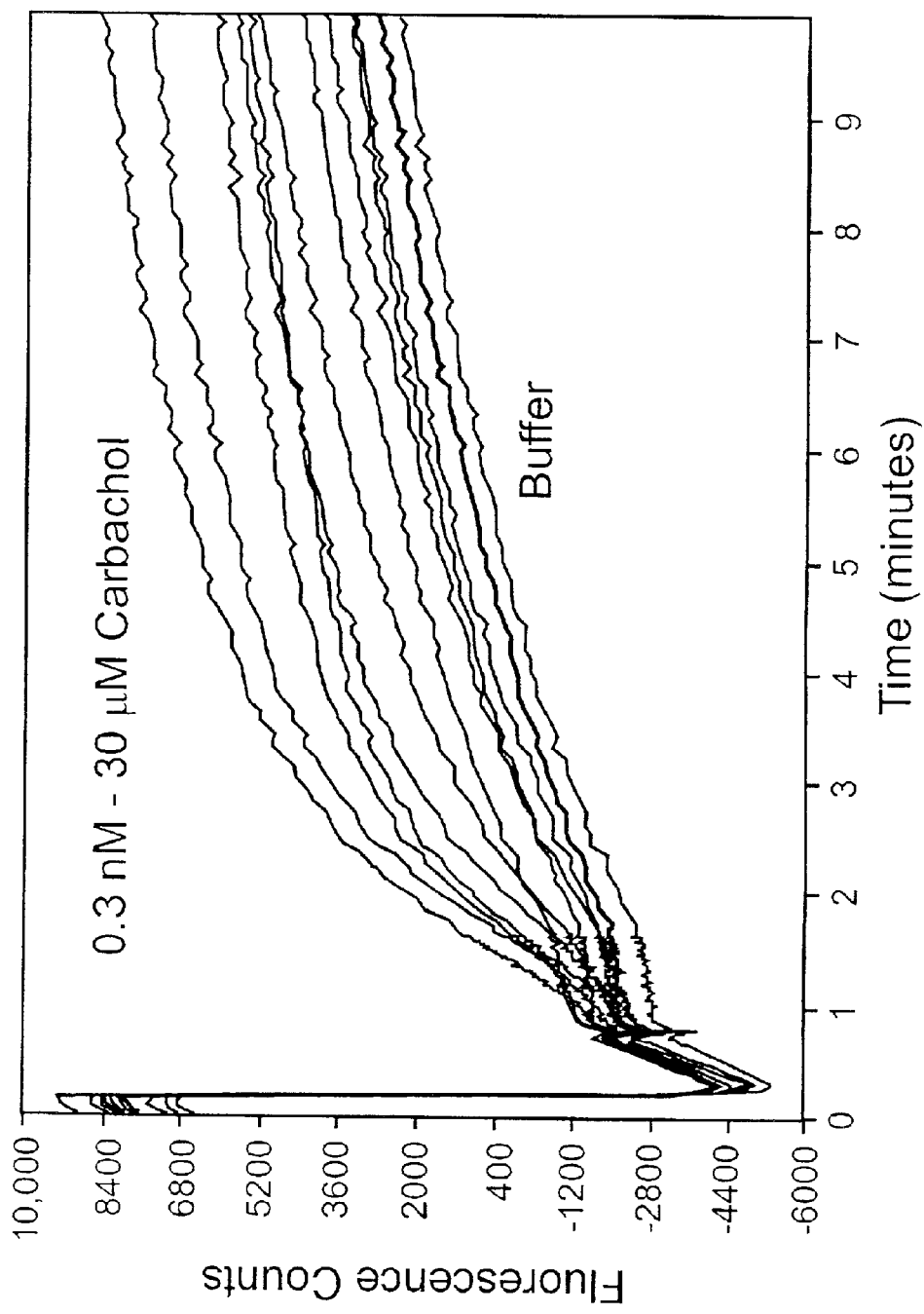
FIG. 3 shows the fluorescence response of Compound 8 to intracellular pH changes in CHO-M1 cells upon the addition of various amounts of carbachol (as described in Example 16).

FIG. 3 shows that dose-dependent intracellular pH changes are observed when the CHO-M1 cells, expressing the human muscarinic receptor M1, are treated with various concentrations of carbachol.

Figure 4:
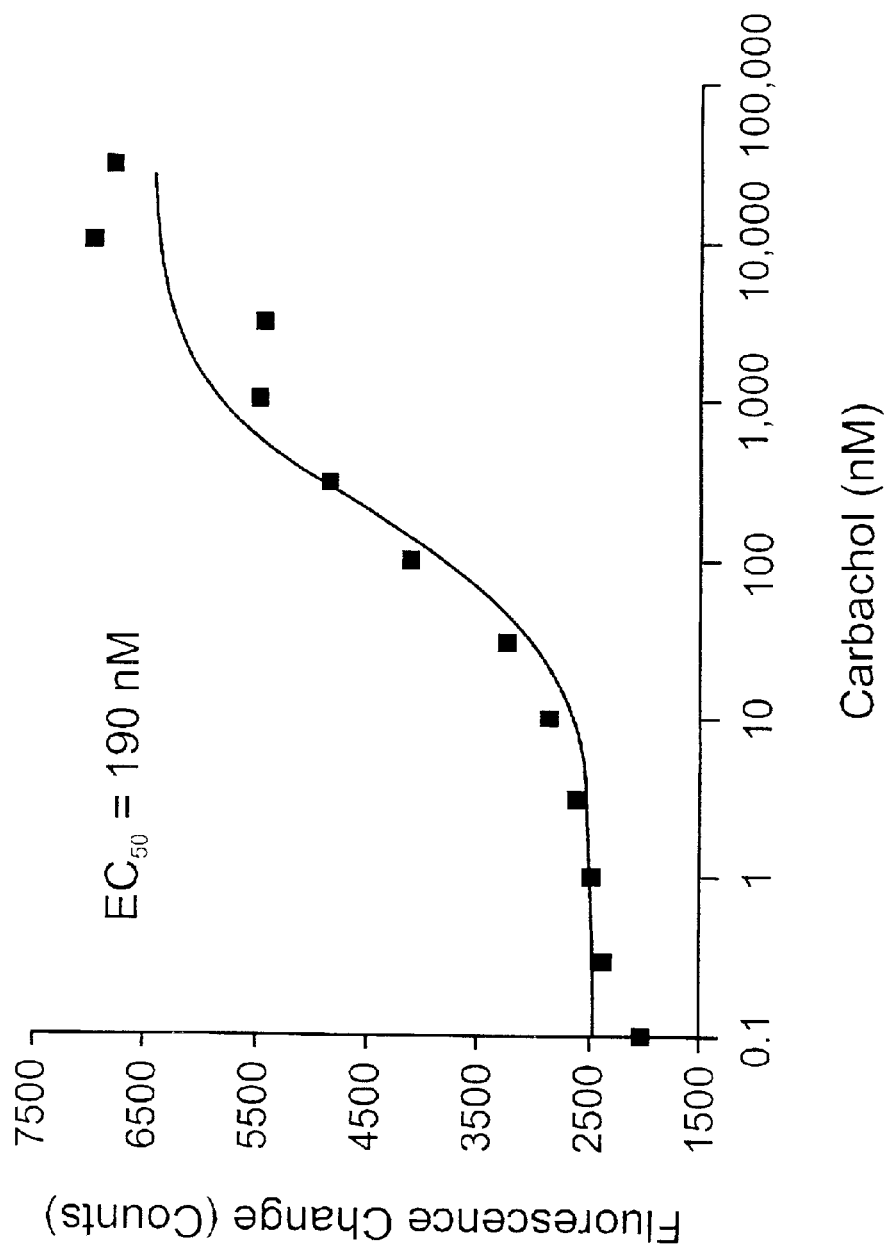
FIG. 4 shows the calculation of the $EC_{50}$ of carbachol in CHO-M1 cells, as determined by monitoring the intracellular pH dose-response with Compound 5, 8, or 20 (as described in Example 16).

FIG. 4 shows that the $EC_{50}$ (effective concentration of the drug that causes 50% of the maximum response) of the carbachol response is about 190 nM.

Example 17
Monitoring Intracellular pH Fluctuations Using Compounds 5, 8, and 20 in Combination With a Microscope Compounds 5, 8, and 20 are used to monitor intracellular pH fluctuations in biological samples using a microscope, for example, using procedures described in the following references, each of which is incorporated herein by reference: (1) Bonanno, J. A. and T. E. Machen, "Intracellular pH regulation in basal corneal epithelial cells measured in corneal explants: characterization of Na/H exchange" (*Exp. Eye Res.* 49(1): 129–42 (1989)); (2) Boyarsky, G. et al., "Inadequacy of high K+/nigericin for calibrating BCECF. I. Estimating steady-state intracellular pH" (*Am. J. Physiol.* 271(4 Pt 1): C1131–45 (1996)); (3) Lanz, E. et al., "2',7'-bis-(2-carboxyethyl)-5(6)-carboxyfluorescein as a dual-emission fluorescent indicator of intracellular pH suitable for argon laser confocal microscopy" (*Folia Microbiol.* 44(4): 429–34 (1999)); and (4) Weinlich, M. et al., "Intracellular pH-measurements in rat duodenal mucosa in vitro using confocal laserscan microscopy" (*Z. Gastroenterol.* 35(4): 263–70 (1997)).

Example 18
Monitoring Intracellular pH Fluctuations Using Compounds 5, 8, and 20 in Combination With a Flow Cytometer Compounds 5 and 8 are used to monitor intracellular pH fluctuations using a flow cytometer, for example, using procedures described in the following references, each of which is incorporated herein by reference: (1) Radosevic, K. et al., "Changes in intracellular calcium concentration and pH of target cells during the cytotoxic process: a quantitative study at the single cell level" (*Cytometry* 20(4): 281–9 (1995)); (2) Franck, P. et al., "Measurement of intracellular pH in cultured cells by flow cytometry with BCECF-AM" (*J. Biotechnol.* 46(3): 187–95 (1996)); and (3) Olson, D. P. et al., "Detection of MRP functional activity: calcein AM but not BCECF AM as a Multidrug Resistance-related Protein (MRP1) substrate" (*Cytometry* 46(2): 105–13 (2001)).

Example 19
Human Muscarinic Receptor M1 Assay

CHO-M1 cells are CHO-K1 cells stably transfected with the human muscarinic receptor M1. These cells are propagated and maintained in HAM's F-12 medium containing 10% FCS, 1× Pen/Strep, and 2 mM L-glutamine. The assay is performed according to the following procedure:

The CHO-M1 cells are plated at 60,000 cells per well in 40 µL medium for 96-well plates. The cells are then incubated in a 37° C. $CO_2$ incubator overnight.

A 10 mM stock solution of an appropriate pH indicator is prepared. For example, 5.9 mg of one of Compounds 5, 8, 19, or 20 is dissolved in 1 mL DMSO. A 25 mM stock solution of an appropriate Masking Compound (as described in Example 25) is prepared by dissolving an appropriate amount of compound in 10 mL water. A 250 mM stock solution of probenecid is prepared by dissolving 0.71 g of probenecid in 5 mL of 1 M NaOH, then adding 5 mL 1× Assay Buffer (1× Hanks' Balanced Saline Solution+20 mM HEPES, pH 7.4) and mixing well.

A 5× Loading Buffer is prepared by adding 6 µL of the 10 mM stock solution of Compound 5, 8, 19, or 20, 0.3 mL of 25 mM Masking Compound and 60 µL of 250 mM probenecid to 0.834 mL 1× Assay Buffer.

The cell plate is removed from the incubator. To each well is added 10 µL of 5× Loading Buffer. The cells are then incubated at room temperature for 1 hour, after which 5 µL of 220 mM $NH_4Cl$ (11×) solution in 1× H+H buffer+2.5 mM probenecid is added to each well, and the cells are incubated for an additional 15 minutes at room temperature.

A compound plate is prepared in 1× H+H Buffer+2.5 mM probenecid prior to running the multiwell microplate assay. A 55.5 mM stock solution is prepared by dissolving 4.6 mg of carbachol in 1 mL of 1× assay buffer. The stock solution is then diluted to prepare a series of carbachol solutions having final concentrations of 0.03, 0.08, 0.2, 0.7, 2, 6, and 20 µM, respectively. A minimum of 250 µL of the selected carbachol solution is transferred to each well of a compound plate using the fluidics module of a multiwell microplate reader, and subsequent fluorescence readings are recorded.

Figure 5:
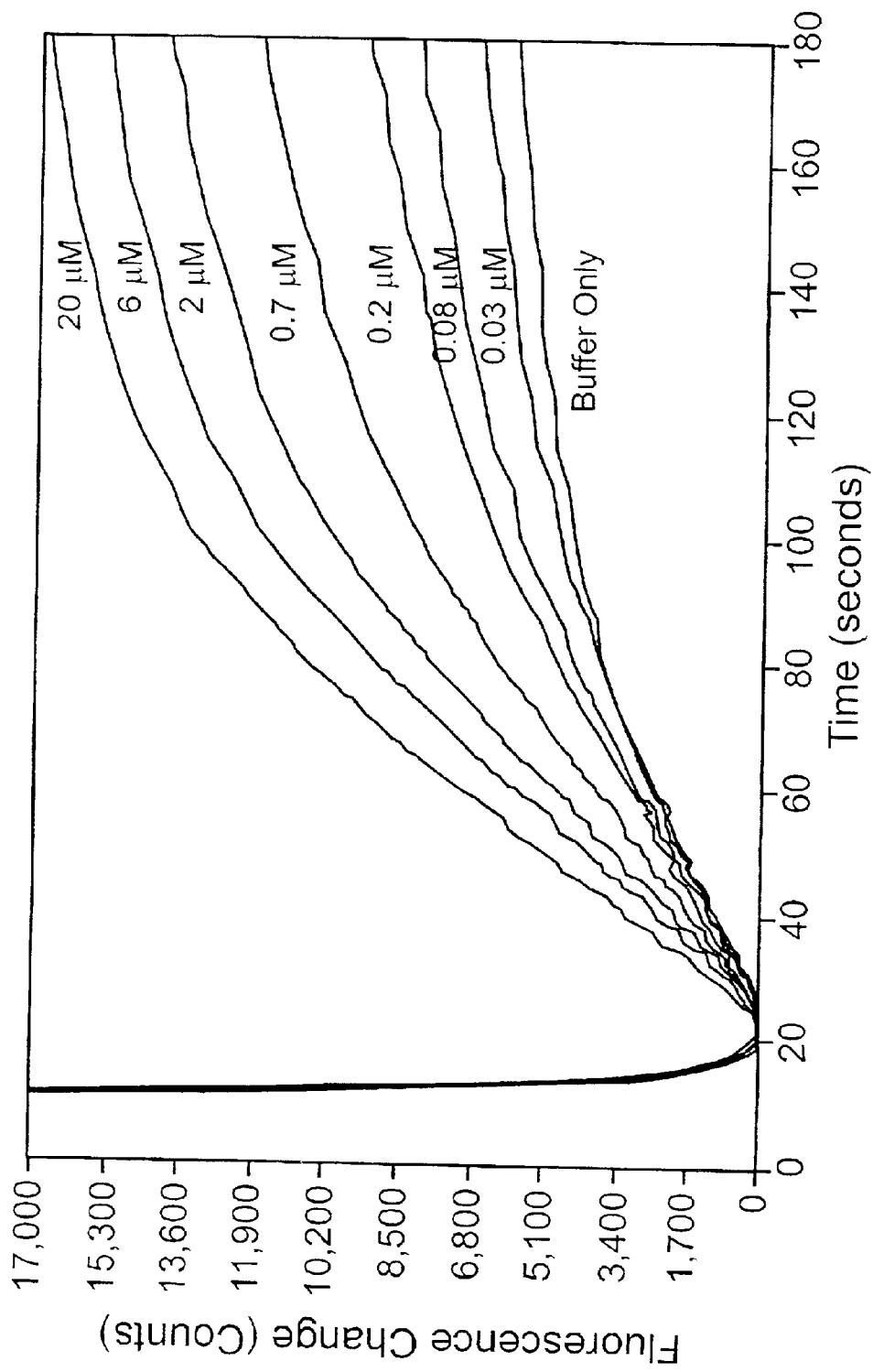
FIG. 5 shows the effect of increasing concentrations of carbachol on M1CHO cells, as determined by monitoring the intracellular pH dose-response with Compound 5, 8, or 20 (as described in Example 19)

FIG. 5 shows the exemplary results. The drop in fluorescence observed at from 10 to 20 seconds is due to the increased acidification of the sample cells (resulting in a decrease in fluorescence). The low pH stimulates the Na+/

H+ exchange pump. The presence of carbachol increases the activity of the pump, resulting in a greater alkalinization of the cells in a dose dependent manner (n=12/group)

Example 20
Drug Resistance Assay

MCF7/ADR cells are MCF7 mammary gland adenocarcinoma selected for adriamycin resistance. These cells are propagated and maintained in DMEM medium containing 5% FCS, 1× Pen/Strep, 2 mM L-glutamine, and non-essential amino acids. The assay is performed according to the following procedure.

The MCF7/ADR cells are plated at 25,000 cells per well in 40 µL medium for 96-well plates. The cells are then incubated in a 37° C. $CO_2$ incubator overnight.

A 10 mM stock solution of an appropriate pH indicator is prepared. For example, 5.9 mg of one of Compounds 5, 8, 19, or 20 is dissolved in 1 mL DMSO. A 25 mM stock solution of a Masking Compound is prepared by dissolving an appropriate amount of the desired Masking Compound in 10 mL water. A 250 mM stock solution of probenecid is prepared by dissolving 0.71 g of probenecid in 5 mL of 1 M NaOH, then adding 5 mL 1× Assay Buffer (1× Hanks' Balanced Saline Solution+20 mM HEPES, pH 7.4) and mixing well.

A 5× Loading Buffer is prepared by adding 6 µL of the 10 mM stock solution of Compound 5, 8, 19, or 20, 0.3 mL of 25 mM Masking Compound and 60 µL of 250 mM probenecid to 0.834 mL 1× Assay Buffer.

The cell plate is removed from the incubator, and all wells are washed once with 1× Assay Buffer, leaving 40 µL of buffer in each well. The cell plate is then incubated at 37° C. for at least 4 hours. To each well is added 10 µL of 5× Loading Buffer, and the cells are incubated at room temperature for 1 additional hour.

After 1 hour, 5 µL of 220 mM $NH_4Cl$ is added to each well, and the cells are incubated at room temperature for an additional 15 minutes.

A compound plate is prepared in 1× H+H Buffer+2.5 mM probenecid prior to running the multiwell microplate assay. A stock solution of insulin is prepared by dissolving 1 mg of insulin in 1 mL of 1 M HCl to a concentration of 174 µM. A 5 µL aliquot of the insulin stock solution is diluted with 4,574 µL H+H/2 mM probenecid/0.1%BSA solution (190 nM stock, 150 nM final concentration). Three-fold dilutions are performed 11 times to obtain final concentrations of 0.003, 0.008, 0.02, 0.07, 0.2, 0.6, 1.9, 5.6, 17, 50, and 150 nM, respectively. A minimum of 250 µL of the selected dilute insulin solution is added to each well of the compound plate using the fluidics module of a multiwell microplate reader, and subsequent fluorescence readings are recorded.

Figure 6:
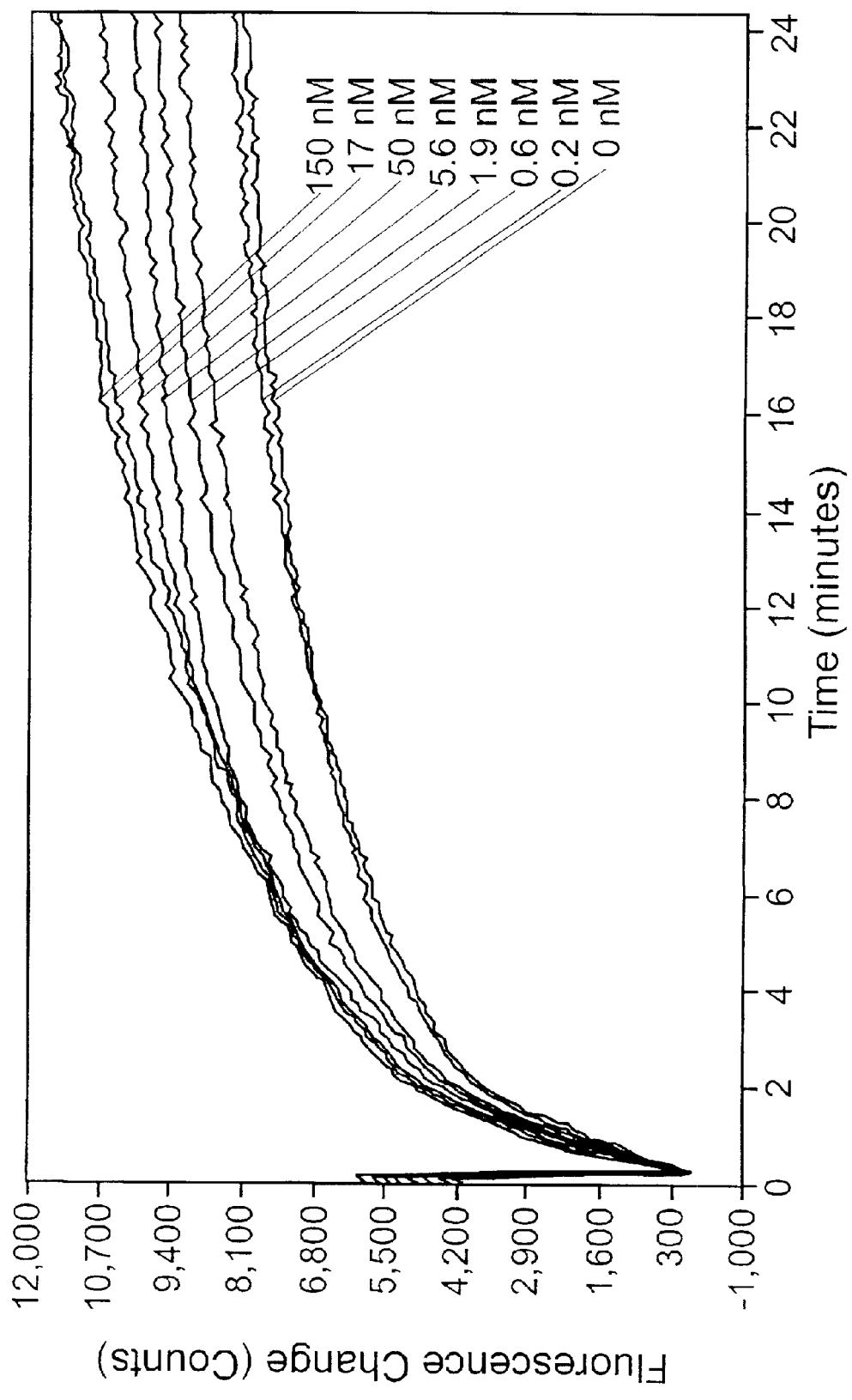
FIG. 6 shows the effect of increasing concentrations of insulin on MCF7/ADR cells, as determined by monitoring the intracellular pH dose-response with Compound 5, 8, or 20 (as described in Example 20).

FIG. 6 shows exemplary results. The drop is fluorescence signal observed at 10 to 20 seconds corresponds to an increased acidification of the cells. The low cellular pH stimulates the Na+/H+exchange pump. The presence of insulin increases the activity of the pump, resulting in a greater alkalinization of the cells in a dose-dependent manner (n=4/group).

Example 21
Pirenzapine Inhibits Carbachol-Mediated Stimulation of M1CHO Cells M1CHO Cells, 50,000, in 40 µL are seeded and incubated at 37° C., 5% $CO_2$ overnight in a 96-well microplate. To each well is added 10 µL of the Loading Buffer (as described in Examples 19 and 20) including a fluorescein diacetate compound of the invention and a nonfluorescent quenching dye. After 45 min at room temperature 5 µL of 220 mM ammonium chloride, in combination with pirenzapine to a final concentration of 0.01 µM, 1.0 µM, 0.3 µM, and 0.1 µM. Following an additional 15 min incubation at room temperature, 200 µL of buffer containing carbachol at a final concentration of 1 µM or 'Buffer Only' is added using the fluidics module of a fluorescence microplate reader (10 seconds after the start of the experiment) and fluorescence readings are taken. A drop in fluorescence signal is observed at time=10 to 20 seconds, corresponding to a drop in signal due to the increased acidification of the cells. The low pH stimulates the $Na^+/H^+$ exchange pump. Pirenzapine inhibits the carbachol-mediated stimulation of 1 µM carbachol (n=6/group).

Example 22
Effect of Increasing Concentrations of RANTES on CHO/CCR5/Galphaqi5 Cells CHO/CCR5/Galphaqi5 cells, 80,000, in 40 µL are seeded and incubated at 37° C., 5% $CO_2$ overnight in a 96-well microplate. To each well is added 10 µL of Loading Buffer (as described in Examples 19 and 20) including a fluorescein diacetate compound of the invention and a nonfluorescent quenching dye. After 45 min at room temperature 5 µL of 220 mM ammonium chloride is added. Following an additional 15 min incubation at room temperature, 200 µL of buffer containing RANTES to a final concentration of 500, 167, 56, 19, 6, 2, or 0 nM is added using the fluidics module on a fluorescence microplate reader (10 seconds after the start of the experiment) and fluorescence readings are recorded. A drop in fluorescence signal is observed at time=10 to 20 seconds, corresponding to an increased acidification of the cells. The low pH stimulates the Na+/H+ exchange pump. The presence of RANTES increases the activity of the pump, resulting in a greater alkalinization of the cells in a dose:dependent manner (n=3/group).

Example 23
The Effect of Increasing Concentrations of Carbachol on M1CHO Cells M1CHO cells, 50,000, in 40 µL were seeded and incubated at 37° C., 5% $CO_2$ overnight in a 96-well microplate. To each well is added 10 µL of the Loading Buffer (as described in Examples 19 and 20) including a fluorescein diacetate compound of the invention and a nonfluorescent quenching dye. After 45 min at room temperature, 5 µL of 220 mM ammonium chloride is added. Following an additional 15 min incubation at room temp 200 µL of buffer containing carbachol at 6.7 µM or 0 µM are added using the fluidics module of a fluorescence microplate reader (15 sec after the start of the experiment) and fluorescence readings are taken. A drop is fluorescence signal is observed at time=10 to 20 seconds due to the increased acidification of the cells. The low pH stimulates the $Na^+/H^+$ exchange pump. The presence of carbachol increases the activity of the pump, resulting in a greater alkalinization of the cells in a dose:dependent manner.

The effect of carbachol can also be monitored by plotting the ratio of the emission intensity to excitation intensity. For Compounds 19 and 20, emission is monitored at 550 nm and excitation is monitored at 505 and 470 nm.

Example 24
Preparation of Conjugates of the Compounds of the Invention

Compounds 6, 12, and 14 are used to prepare a variety of 2',7'-diethyl-5-(or 6-) carboxyfluorescein bioconjugates of proteins (such as avidin, antibodies, transferrin, etc.), carbohydrates, nucleic acids, biotin, amino-substituted polyethylene glycols, and amino-substituted dextrans and microspheres, for example, utilizing the techniques described in *Bioconjugate Techniques*, G. T. Hermanson (Academic Press, 1996), which is incorporated herein by reference.

Example 25
Reduction of Extracellular and/or Background Fluorescence

The assays of the invention optionally may be performed using systems for reducing extracellular and/or background fluorescence, including separating layers and/or masking compounds. These systems may be particularly useful in assays of intracellular pH, where they may be used to reduce detection of fluorescence from indicator dyes that have leaked from the cell interior into the extracellular medium.

A separating layer generally comprises any material that separates labeled cells from the majority of the extracellular medium (typically by being positioned between the labeled cells and the majority of the extracellular medium) and that reduces detection of light from the majority of the extracellular medium. The separating layer may reduce the detection of undesired light using any suitable mechanism, including (1) absorbing and/or reflecting excitation light before it excites extracellular fluorophores, and/or (2) absorbing and/or reflecting fluorescence emitted by extracellular fluorophores. Exemplary separating layers may include (1) a thin film or coating of metal, beads, or other absorbent and/or reflective materials, which typically is permeable to the extracellular medium, and/or (2) a sample container insert that displaces medium away from the cells, which typically is impermeable to the extracellular medium. Exemplary separating layers are disclosed in the following materials, which are incorporated herein by reference: U.S. Pat. No. 5,601,997, issued Feb. 11, 1997; and PCT Patent Application Serial No. PCT/EP97/02662, filed May 23, 1997.

A masking (or photon-reducing) compound generally comprises any composition such as a molecule or particle that reduces the amount of light detected from fluorescent materials in the extracellular medium. The masking compound may reduce the amount of light using any suitable mechanism, including (1) absorbing excitation light before it excites extracellular fluorophores, (2) reducing and/or quenching the fluorescence of the extracellular fluorophores (e.g., by reducing their extinction coefficients and/or quantum yields), and/or (3) absorbing fluorescence emitted by the extracellular fluorophores, among others.

Exemplary masking compounds may include (1) binding partners, such as antibodies, (2) paramagnetic ions, such as $Mn^{2+}$, $Co^{2+}$, or $Cu^{2+}$, (3) quenchers, such as static and dynamic quenchers, (4) energy transfer partners, such as complementary acceptors, and/or (5) dyes (including pigments) having overlapping spectra or that are otherwise capable of accepting energy transfer from a fluorescent compound of the invention, among others. Dyes having overlapping spectra may include (1) acid dyes (e.g., sulphan blue, acid violet, acid red, amido black, brilliant blue R, azocarmine G, xylidine P. 2R, orange G, and erythrosine, among others), (2) direct dyes (e.g., trypan blue, Evans blue, vital red, thiazine red, and Congo red, among others), (3) basic dyes (e.g., crystal violet, nightblue, malachite green, methylene blue, toluidine blue, azur A, Victoria blue, Nile blue, rhodanile blue, safranin, neutral red, and rosaniline, among others), and/or (4) other dye groups (e.g., celestine blue, Alcian blue, carminic acid, haematoxylin, and phenol red, among others), among others.

In one aspect of the invention, the masking compound includes one or more of Acid Blue 45, Acid Blue 92, Acid Blue 93, Acid Green 25, Acid Red 106, Acid Red 112 (Ponceau S), Acid Red 40, Acid Violet 5, Acid Violet 7, Alcian Blue 8GX, Amaranth, Brilliant Black BN, Brompyrogallol Red, Direct Blue 71, Direct Red 75, Direct Violet 51, Erioglaucine (Food Dye Blue), Erythrosin B, Gallocyanine, Hydroxy Naphthol Blue, Indigo Carmine, Malachite Green, Phenol Red, Potassium Ludigotrisulfonate, QSY-7, Reactive Black 5, Reactive Blue 2, Sufonazo III, and Violamine R. Additional exemplary masking compounds, as well as methods of use, are disclosed in the following materials, which are incorporated herein by reference: U.S. Pat. No. 6,200,762, issued Mar. 13, 2001; U.S. Pat. No. 6,214,563, issued Apr. 10, 2001; U.S. Pat. No. 6,221,612, issued Apr. 24, 2001; and PCT Patent Application Serial No. PCT/EP97/02662, filed May 23, 1997.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. These claims may refer to "an" element or "a first" element or the equivalent thereof; such claims should be understood to include incorporation of one or more such elements, neither requiring nor excluding two or more such elements. Inventions embodied in other combinations and subcombinations of features, functions, elements, and/or properties may be claimed in nonprovisional applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A compound having the formula

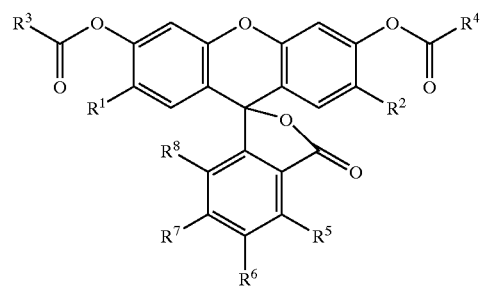

wherein $R^1$ and $R^2$ are independently $C_1$–$C_{12}$ alkyl that is optionally substituted one or more times by $C_1$–$C_6$ alkoxy or halogen, provided that the alpha-carbon of the alkyl is not halogenated;

$R^3$ and $R^4$ are independently $C_1$–$C_6$ alkyl; and $R^5$–$R^8$ are independently hydrogen, halogen, $C_1$–$C_6$ alkyl, $C_1$–$C_6$ alkoxy, sulfonic acid, ester of sulfonic acid, carboxylic acid, ester of carboxylic acid, —L—$R_X$, or —L—$S_C$, where L is a covalent linkage, $R_X$ is a reactive functional group, and $S_C$ is a conjugated substance;

provided that at least one of $R^5$–$R^8$ is sulfonic acid, ester of sulfonic acid, carboxylic acid, ester of carboxylic acid, —L—$R_X$, or —L—$S_C$.

2. The compound of claim 1, wherein $R^1$ and $R^2$ are independently $C_1$–$C_6$ alkyls.

3. The compound of claim 1, wherein each of $R^1$, $R^2$, $R^3$, and $R^4$ is independently methyl or ethyl.

4. The compound of claim 1, wherein one of $R^6$ and $R^7$ is nonhydrogen.

5. The compound of claim 4, wherein one of $R^6$ and $R^7$ is sulfonic acid, ester of sulfonic acid, carboxylic acid, ester of carboxylic acid, —L—$R_X$, or —L—$S_C$.

6. The compound of claim 5, wherein one of $R^6$ and $R^7$ is a protected sulfonic acid or a protected carboxylic acid.

7. The compound of claim 1, wherein one of $R^6$ and $R^7$ is —L—$R_X$ or —L—$S_C$.

8. The compound of claim 1, wherein L is a single bond or a covalent linkage that incorporates 1–20 nonhydrogen atoms.

9. The compound of claim 8, wherein L comprises one or more carbon-carbon bonds, amide linkages, ester linkages, sulfonamide linkages, ether linkages, or thioether linkages, or a combination thereof.

10. The compound of claim 1, wherein $R_X$ is an activated ester of a carboxylic acid, an aldehyde, an alkyl halide, an amine, an anhydride, an aryl halide, a carboxylic acid, a haloacetamide, a halotriazine, a hydrazine, an isocyanate, an isothiocyanate, a maleimide, a phosphoramidite, a sulfonyl halide, or a thiol.

11. The compound of claim 10, wherein $R_X$ is an activated ester of a carboxylic acid, an amine, a haloacetamide, a hydrazine, an isothiocyanate, or a maleimide.

12. The compound of claim 11, wherein $R_X$ is a succinimidyl ester of a carboxylic acid.

13. The compound of claim 1, wherein $S_C$ is a member of a specific binding pair, molecular carrier, or a solid or semi-solid matrix.

14. The compound of claim 1, wherein $S_C$ is an amino acid, a peptide, a protein, a nucleoside, a nucleotide, an oligonucleotide, a nucleic acid polymer, or a carbohydrate.

15. The compound of claim 1, wherein $S_C$ is a polar moiety or a polar moiety that has been esterified.

16. The compound of claim 15, where the polar moiety is protected by acetoxymethyl esters.

17. The compound of claim 1, wherein $S_C$ is an antibody, a dextran, or a nitrilotriacetic acid.

18. The compound of claim 1, wherein
$R^1$ and $R^2$ are each ethyl;
$R^3$ and $R^4$ are each methyl; and
one of $R^6$ and $R^7$ is sulfonic acid, ester of sulfonic acid, carboxylic acid, ester of carboxylic acid, —L—$R_X$, or —L—$S_C$.

19. A compound having the formula

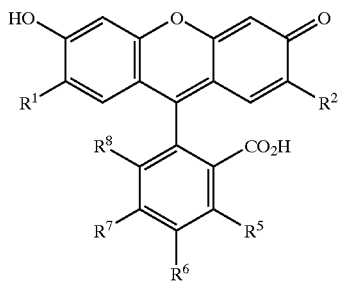

wherein $R^1$ and $R^2$ are independently $C_1$–$C_{12}$ alkyl that is optionally substituted one or more times by $C_1$–$C_6$ alkoxy or halogen, provided that the alpha-carbon of the alkyl is not halogenated; and $R^5$–$R^8$ are independently hydrogen, halogen, $C_1$–$C_6$ alkyl, $C_1$–$C_6$ alkoxy, sulfonic acid, ester of sulfonic acid, carboxylic acid, ester of carboxylic acid, —L—$R_X$, or —L—$S_C$, where L is a covalent linkage, $R_X$ is a reactive functional group, and $S_C$ is a conjugated substance;

provided that at least one of $R^5$–$R^8$ is sulfonic acid, ester of sulfonic acid, carboxylic acid, ester of carboxylic acid, —L—$R_X$, or —L—$S_C$.

20. The compound of claim 19, wherein $R^1$ and $R^2$ are independently $C_1$–$C_6$ alkyls; and each of $R^1$, and $R^2$ is independently methyl or ethyl.

21. The compound of claim 19, wherein one of $R^6$ and $R^7$ is sulfonic acid, carboxylic acid, —L—$R_X$, or —L—$S_C$.

22. The compound of claim 19, wherein L is a single bond or a covalent linkage that incorporates 1–20 nonhydrogen atoms.

23. The compound of claim 19, wherein $R_X$ is an activated ester of a carboxylic acid, an aldehyde, an alkyl halide, an amine, an anhydride, an aryl halide, a carboxylic acid, a haloacetamide, a halotriazine, a hydrazine, an isocyanate, an isothiocyanate, a maleimide, a phosphoramidite, a sulfonyl halide, or a thiol.

24. The compound of claim 23, wherein $R_X$ is a succinimidyl ester of a carboxylic acid, an amine, an iodoacetamide, a hydrazine, an isothiocyanate, or a maleimide.

25. The compound of claim 19, wherein $S_C$ is a member of a specific binding pair.

26. The compound of claim 19, wherein $S_C$ is an amino acid, a peptide, a protein, a nucleoside, a nucleotide, an oligonucleotide, a nucleic acid polymer, or a carbohydrate.

27. The compound of claim 19, wherein $R^1$ and $R^2$ are each ethyl, and one of $R^6$ and $R^7$ is sulfonic acid, ester of sulfonic acid, carboxylic acid, ester of carboxylic acid, —L—$R_X$, or —L—$S_C$.

28. A kit, comprising a compound having the formula wherein $R^1$ and $R^2$ are independently $C_1$–$C_{12}$ alkyl that are optionally substituted one or more times by $C_1$–$C_6$ alkoxy or halogen, provided that the alpha-carbon of the alkyl is not halogenated;

$R^3$ and $R^4$ are independently $C_1$–$C_6$ alkyl; and $R^5$–$R^8$ are independently hydrogen, halogen, $C_1$–$C_6$ alkyl, $C_1$–$C_6$ alkoxy, sulfonic acid, ester of sulfonic acid, carboxylic acid, ester of carboxylic acid, —L—$R_X$, or —L—$S_C$, where L is a covalent linkage, $R_X$ is a reactive functional group, and $S_C$ is a conjugated substance;

provided that at least one of $R^5$–$R^8$ is sulfonic acid, ester of sulfonic acid, carboxylic acid, ester of carboxylic acid, —L—$R_X$, or —L—$S_C$.

29. The kit of claim 28, further comprising at least one additional reagent.

30. The kit of claim 29, wherein the additional reagent is a buffering agent, a fluorescence calibration standard, an enzyme, an enzyme substrate, a nucleic acid stain, or a labeled antibody.

31. The kit of claim 28, further comprising a substantially cell-impermeant dye having an appropriate absorbance spectrum to accept fluorescence energy transfer from a product resulting from esterase activity on the compound.

32. The kit of claim 28, wherein $R^1$ and $R^2$ are independently methyl or ethyl; $R^3$ and $R^4$ are each methyl; and at least one of $R^6$ and $R^7$ is —L—$R_X$ or —L—$S_C$.

33. The kit of claim 32, wherein one of $R^6$ and $R^7$ is —(CO$_2$)—CH$_2$—(O$_2$C)—CH$_3$, and the rest of $R^5$–$R^8$ are hydrogen.

34. The kit of claim 28, wherein the kit is configured for use in conjunction with a sample in a multiwell microplate or a microfluidic chip.

* * * * *